US012681021B2

(12) United States Patent
Cournoyer et al.

(10) Patent No.: US 12,681,021 B2
(45) Date of Patent: Jul. 14, 2026

(54) MULTIPLEXED EXTERNAL CALIBRATOR AND CONTROL FOR SCREENING AND DIAGNOSTIC ASSAYS

(71) Applicant: DH TECHNOLOGIES DEVELOPMENT PTE. LTD., Singapore (SG)

(72) Inventors: Jason Cournoyer, Jamaica Plain, MA (US); Subhakar Dey, Lexington, MA (US); Amy E. Trudel, Nashua, NH (US); Subhasish Purkayastha, Framingham, MA (US)

(73) Assignee: DH TECHNOLOGIES DEVELOPMENT PTE. LTD., Singapore (SG)

( * ) Notice: Subject to any disclaimer, the term of this patent is extended or adjusted under 35 U.S.C. 154(b) by 1065 days.

(21) Appl. No.: 17/419,844

(22) PCT Filed: Oct. 16, 2019

(86) PCT No.: PCT/IB2019/058827
§ 371 (c)(1),
(2) Date: Jun. 30, 2021

(87) PCT Pub. No.: WO2020/079614
PCT Pub. Date: Apr. 23, 2020

(65) Prior Publication Data

US 2022/0308066 A1 Sep. 29, 2022

Related U.S. Application Data

(60) Provisional application No. 62/869,689, filed on Jul. 2, 2019, provisional application No. 62/788,514, filed
(Continued)

(51) Int. Cl.
*G01N 30/86* (2006.01)
*G01N 33/68* (2006.01)
(Continued)

(52) U.S. Cl.
CPC ......... *G01N 33/6848* (2013.01); *G01N 33/74* (2013.01); *G01N 30/8682* (2013.01); *G01N 2458/15* (2013.01)

(58) Field of Classification Search
CPC ............... G01N 33/6848; G01N 33/74; G01N 30/8682; G01N 2458/15; G01N 33/743; C07J 41/0016; H01J 49/0009
See application file for complete search history.

(56) References Cited

U.S. PATENT DOCUMENTS 11,105,814 B2 * 8/2021 LeBlanc ............ G01N 33/6848
11,442,046 B2 9/2022 Carell et al.
(Continued)

FOREIGN PATENT DOCUMENTS

EP 3004861 A1 4/2016
WO 20090141310 A1 11/2009
(Continued)

OTHER PUBLICATIONS

International Search Report and Written Opinion for PCT/IB2019/058827 mailed Mar. 18, 2020.
(Continued)

*Primary Examiner* — Rebecca M Fritchman
(74) *Attorney, Agent, or Firm* — Potomac Law Group, PLLC; Reza Mollaaghababa; Ido Rabinovitch

(57) ABSTRACT

Methods, compositions, kits, and apparatuses for MS-based quantification of a target analyte (e.g., a peptide, a hormone) in a sample are provided for increasing the productivity and/or throughput of samples by reducing the time and/or cost associated with conventional techniques for external instrument calibration that typically utilize a series of calibrators that are sequentially run through the same analytical process as a batch of samples. In various aspects, calibration mixtures are provided containing a known quantity of a
(Continued)

plurality of calibrants for a target analyte of interest, with each calibrant being distinguishable in the calibration mixture by mass spectrometry such that a complete calibration curve can be generated from a single external calibration run.

20 Claims, 18 Drawing Sheets

Related U.S. Application Data on Jan. 4, 2019, provisional application No. 62/746,404, filed on Oct. 16, 2018.

(51) Int. Cl.
*G01N 33/74* (2006.01)
*H01J 49/00* (2006.01)

(56) References Cited

U.S. PATENT DOCUMENTS

| | | | | |
|---|---|---|---|---|
| 2007/0207555 | A1* | 9/2007 | Guerra | C07B 59/008 702/19 |
| 2010/0021938 | A1* | 1/2010 | Boutaud | G01N 33/6896 435/7.92 |
| 2010/0167267 | A1* | 7/2010 | Schulzknappe | G01N 1/28 436/15 |
| 2012/0187284 | A1* | 7/2012 | Geyer | H01J 49/0009 250/252.1 |
| 2013/0277542 | A1* | 10/2013 | Sasaki | H01J 49/0009 250/252.1 |
| 2018/0342381 | A1* | 11/2018 | Rule | H01J 49/0009 |
| 2022/0099637 | A1 | 3/2022 | Gu et al. | |

FOREIGN PATENT DOCUMENTS

| | | | |
|---|---|---|---|
| WO | 2010136455 | A1 | 12/2010 |
| WO | 20120170549 | A1 | 12/2012 |
| WO | 20140197754 | A1 | 12/2014 |
| WO | 20150106169 | A1 | 7/2015 |
| WO | 2021237035 | A1 | 11/2021 |

OTHER PUBLICATIONS

March Raymond E. et al., "Calculation of elemental composition of gaseous ions from stable nuclei signals using high resolution mass spectrometry (HRMS): Examination of the stages involved" International Journal of Mass Spectrometry, Elsevier Science Publishers, vol. 415, Feb. 3, 2017.
Written Opinion for International Application No. PCT/IB2022/062239 mailed Dec. 12, 2023.
Written Opinion for International Application No. PCT/IB2023/059103 mailed Dec. 12, 2023.

* cited by examiner

| (M+2H)²⁺ | Peptide | MRM1 | MRM2 |
|---|---|---|---|
| 636.4 | V I F D A N A P V A V R — m/z = 912.5 (y9); m/z = 1059.6 (y10) | 636.4/1059.6 | 636.4/912.5 |
| 639.4 | V^ I F D A N A P V A V R — m/z = 912.5 (y9); m/z = 1059.6 (y10) | 639.4/1059.6 | 639.4/912.5 |
| 641.4 | V I F D A N A P V A V R^ — m/z = 922.5 (y9); m/z = 1069.6 (y10) | 641.4/1069.6 | 641.4/922.5 |
| 644.4 | V^ I F D A N A P V A V R^ — m/z = 922.5 (y9); m/z = 1069.6 (y10) | 644.4/1069.6 | 644.4/922.5 |
| 647.4 | V^ I F D A N A P V A V^ R^ — m/z = 928.5 (y9); m/z = 1075.6 (y10) | 647.4/1075.6 | 647.4/928.5 |
| 650.4 | V^ I F D A N A P V^ A V^ R^ — m/z = 934.5 (y9); m/z = 1081.6 (y10) | 650.4/1081.6 | 650.4/934.5 |

^ = amino acid with incorporated stable isotope

Peptide concentrations in test solution

| Peptide | nmol/L | Peptide | nmol/L |
|---|---|---|---|
| VIFDANAPVAVR | 12 | FSPDDSAGASALLR^ | 7 |
| VIFDANAPVAVR^ | 18 | FSPDDSAGASALLR | 12 |
| V^IFDANAPVAVR^ | 32 | FSP^DDSAGASAL^L^R^ | 59 |
| V^IFDANAPVAV^R^ | 50 | FSP^DDSAGASALLR | 71 |
| V^IFDANAPVAVR | 107 | FSP^DDSAGASALL^R^ | 126 |
| V^IFDANAPV^AV^R^ | 214 | FSP^DDSAGASALLR^ | 230 |

^ = amino acid with incorporated stable isotope

FIG. 10

Proposed workflow for measuring thyroglobulin by LC-MS/MS using a multiplexed calibrator L1 - FSPDDSAGASALLR
L2 - FSP^DDSAGASALLR
L3 - FSPDDSAGASALLR^
L4 - FSP^DDSAGASALLR^
L5 - FSP^DDSAGASALL^R^
L6 - FSP^DDSAGASAL^L^R^ increasing concentration

L1 - VIFDANAPVAVR
L2 - V^IFDANAPVAVR
L3 - VIFDANAPVAVR^
L4 - V^IFDANAPVAVR^
L5 - V^IFDANAPVAV^R^
L6 - V^IFDANAPV^AV^R^ increasing concentration

^ = amino acid with incorporated stable isotope

12 Peptide Multiplexed Calibrator

+ patient samples

• Addition of IS
• Reduction and alkylation
• Trypsin digestion
• Immunoenrichment for FSP and VIF peptides LC-MS/MS analysis

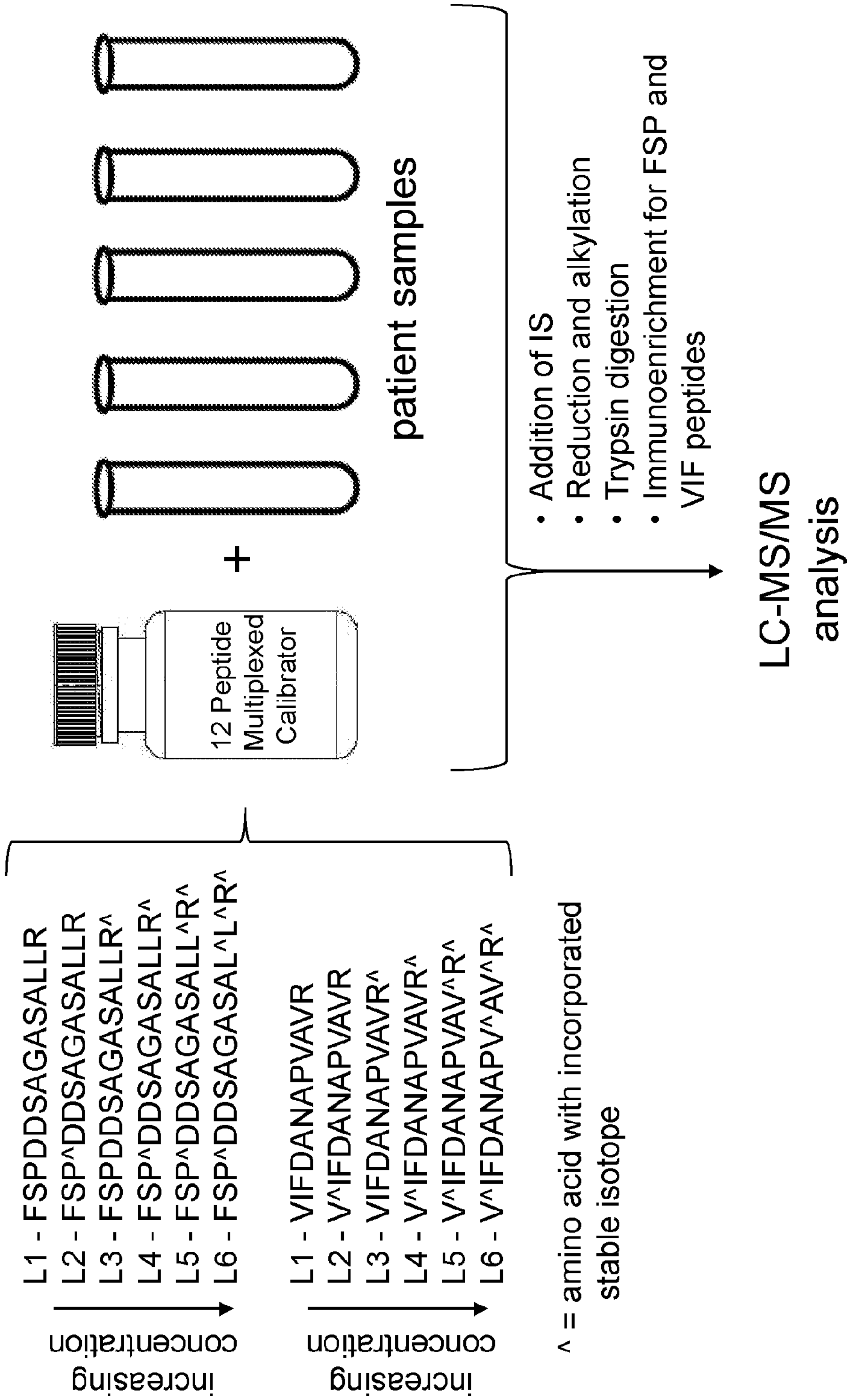

FIG. 13

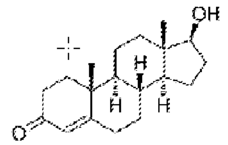
A
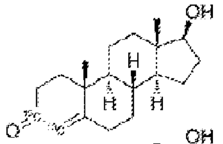
B
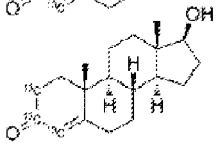
C
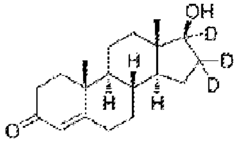
D
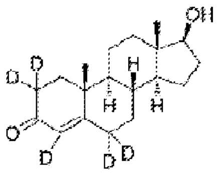
E
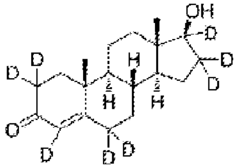
F
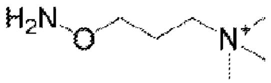
G
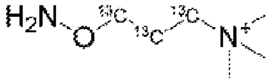
H
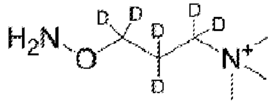
I
| | | Reagents | | |
|---|---|---|---|---|
| Analytes | | G | H | I |
| | A | AG | AH | AI |
| | B | BG | BH | BI |
| | C | CG | CH | CI |
| | D | DG | DH | DI |
| | E | EG | EH | EI |
| | F | FG | FH | FI |
| 18 Combination Analyte and Surrogate Analytes | | | | |
FIG. 17

MULTIPLEXED EXTERNAL CALIBRATOR AND CONTROL FOR SCREENING AND DIAGNOSTIC ASSAYS

RELATED U.S. APPLICATIONS

This application claims the benefit of priority from U.S. Provisional Application No. 62/746,404, filed on Oct. 16, 2018, 62/788,514, filed on Jan. 4, 2019 and 62/869,689, filed on Jul. 2, 2019, the entire contents of all of which is hereby incorporated by reference herein.

FIELD

The present teachings are generally directed to methods, composition, kits, and apparatuses for mass spectrometric analysis of a sample utilizing external calibration for quantifying a target analyte in a separate sample run.

BACKGROUND

Mass spectrometry (MS) is an analytical technique for determining the elemental composition of test substances with both qualitative and quantitative applications. MS can be useful for identifying unknown compounds, determining the isotopic composition of elements in a molecule, determining the structure of a particular compound by observing its fragmentation, and quantifying the amount of a particular compound in a sample. Given its sensitivity and selectivity, MS has been widely used in the fields of chemistry and physics for over a century, and increasingly in biology over the past several decades. Sub-disciplines such as environmental monitoring for pollutants, forensic analysis for drugs of abuse and toxins, biomedical research, clinical disease diagnostics, food analysis, material science, and others, have been utilizing atmospheric pressure ionization mass spectrometers toward great practical value and to help achieve significant advancements in these fields.

For quantification of a target analyte in any sample, instrument calibration is generally required to first establish a relationship between the analytical signal obtained from the particular analytical method used and the quantity of the target analyte in the sample, for example, to account for the effect of the instrument and/or analytical method on the detected quantity of the target analyte. Accordingly, a series of external calibration standards containing a target analyte at multiple different, known concentrations are typically separately and independently run through the analytical method to be applied to the sample in a repeated series of analysis runs prior to going "live" with sample batches. Analysis data from the series of prior calibration runs is used to generate a calibration curve, which may then be used to calculate a concentration of the target analyte in subsequently analyzed samples suspected of containing an unknown concentration of the target analyte.

Furthermore, external calibration is often performed with a series of calibrator standards that resemble samples with regards to an exemplar matrix (e.g., serum, urine), with the known concentrations of the target analyte in each of the plurality of calibrator standards being chosen to span a range that brackets the concentrations believed to be typically found in a batch of samples suspected of containing unknown target analyte concentrations. Generally, external calibration must be performed regularly, e.g., between batches, to minimize potential calibration drift and with the number of calibrator standards being proportional to the accuracy and range required, i.e., assays that require high accuracy over a large concentration range requires many levels of calibrators. By way of example, liquid chromatography-mass spectrometry (LC-MS), which is often used in diagnostic assays due to its ability to provide highly accurate measurements over a large concentration range, can require seven levels of calibrators, with each standard requiring a relatively long analysis time per sample (e.g., greater than 5 minutes for each calibrator adsorbing to and being eluted from a LC column). Accordingly, a substantial portion of total analysis time can be dedicated to external calibration before actual samples with unknown target analyte concentrations are run.

Because a large portion of the total LC-MS/MS analysis time is dedicated to the analysis of calibrators before the samples are even run, conventional external calibration techniques can reduce productivity, increase cost per sample, and render the subsequent analysis of a small batch of samples inefficient.

Accordingly, there is a need for a calibration method that addresses limitations in conventional external calibration methods and processes.

SUMMARY

In accordance with various aspects of the present teachings, methods, compositions, kits, and apparatuses for MS-based quantification of a target analyte (e.g., a peptide, a hormone) in a sample are provided for increasing the productivity and/or throughput of samples by reducing the time and/or cost associated with conventional techniques for external instrument calibration that typically utilize a series of calibrators that are sequentially run through the same analytical process as a batch of samples. In various aspects, calibration mixtures are provided containing a known quantity of a plurality of calibrants selected from the group comprising a standard of a target analyte and one or more stable isotopic analogs of the target analyte, with each of the calibrants in the calibration mixture distinguishable by mass spectrometry such that a complete calibration curve can be generated from a single external calibration run. In various aspects, the plurality of calibrants are distinguished from each other by a mass spectrometer due to differences in their mass (i.e., a difference in mass that can be resolved by a MS instrument), fragmentation pattern, or combinations thereof resulting from the presence of and/or location of different isotopes within various portions of the calibrants. Thus, whereas in a typical, exemplary external calibration protocol in which seven concentrations of standards of the target analyte may be analyzed to establish a calibration curve prior to analyzing the target analyte within a batch of samples, embodiments of the present teachings enable a single calibration mixture containing a plurality of calibrants to be analyzed for the same batch of samples, thereby reducing batch processing time by an amount of time equivalent to six separate and independent analytical runs of the individual calibrator standards. It will be appreciated in light of the present teachings that in addition to this increased throughput, certain embodiments of such methods also decrease the cost per sample and/or enable smaller batches of samples to be more efficiently tested so as to further reduce delays in obtaining diagnostic results. Moreover, in various aspects, the exemplary isotopic calibrants described herein can also be used as internal standards within the samples themselves that can account for matrix effects and/or sample losses during sample preparation. Additionally or alternatively, control solutions including quality control solutions can utilize the exemplary calibrators (e.g., three calibrators can be used as inter-sample controls) to validate instrument calibration over the course of the batch of samples.

In accordance with various aspects of the present teachings, a method of quantifying a target analyte in a series of samples by mass spectrometry is provided that comprises obtaining a mass spectrometer signal for a calibration mixture, wherein the calibration mixture comprises a plurality of calibrants selected from the group comprising a standard of the target analyte, a first isotopic analog of the target analyte, and a second isotopic analog of the target analyte, wherein said plurality of calibrants are distinguishable by mass spectrometry from one another and have different, known concentrations from one another in said calibration mixture. The method also includes identifying from the mass spectrometer signal for the calibration mixture a characteristic response of each of said plurality of calibrants, wherein each of the characteristic responses corresponds to a different one of the plurality of calibrants and the mass spectrometer signal is indicative of the concentration of each of the plurality of calibrants in the calibration mixture. The method further includes generating a single calibration curve for the calibration mixture based on said characteristic responses of said plurality of calibrants. In some embodiments, the method also includes obtaining a mass spectrometer signal from each of the series of samples, identifying from the mass spectrometer signal for each sample a characteristic response indicative of the concentration of the target analyte in each sample, and comparing the characteristic response of the target analyte in each sample to the single calibration curve to quantify the target analyte in each sample.

In some implementations, the calibration mixture comprises different, known concentrations of each of the standard, the first isotopic analog, and the second isotopic analog, and wherein each of the standard, the first isotopic analog, and the second isotopic analog is distinguishable by mass spectrometry from the others. Further, in some related aspects, the calibration mixture comprises at least a third isotopic analog of the target analyte, wherein the third isotopic analog is at a different, known concentration and is distinguishable by mass spectrometry from the standard, the first isotopic analog, and the second isotopic analog. In various implementations, the concentration of the heaviest isotopic analog in the calibration mixture is less than the concentration of the other of said isotopic analogs of said target analyte in the calibration mixture and wherein the concentration of the lightest isotopic analog in the calibration mixture is greater than the concentration of the other of said isotopic analogs of said target analyte in the calibration mixture.

In various implementations, the method further comprises preparing the calibration mixture by combining a known quantity of each of the plurality of calibrants. Additionally or alternatively, the method may comprise adding the calibration mixture to a surrogate sample matrix prior to obtaining the mass spectrometer signal for the calibration mixture. In some related aspects, the plurality of calibrants may be separated from the surrogate sample matrix prior to obtaining the mass spectrometer signal for the calibration mixture. For example, the separation may comprise at least one of solid phase extraction, liquid-liquid extraction, liquid chromatography, gas chromatography, supercritical fluid chromatography, affinity, immunoaffinity, and capillary electrophoresis. In various implementations, the method can also include derivatizing the plurality of calibrants prior to the separation.

In some embodiments, a multiplexed calibration solution may be provided for generating calibration curves for more than one target analyte. For example, in some implementations, the calibration mixture further comprises a set of second calibrants for a second target analyte different from the target analyte, wherein the set of second calibrants comprise at least two of a standard of the second target analyte, a first isotopic analog of the second target analyte, and a second isotopic analog of the second target analyte, wherein said second calibrants are distinguishable by mass spectrometry from one another and have different, known concentrations from one another in said calibration mixture and wherein each of said second calibrants are distinguishable by mass spectrometry from said plurality of calibrants, the method further comprising: identifying from the mass spectrometer signal for the calibration mixture a characteristic response of each of said second calibrants, wherein each of the characteristic responses correspond to a different one of the second calibrants and is indicative of the concentration of the second calibrants in the calibration mixture; generating a second calibration curve based on said characteristic responses of said second calibrants; identifying from the mass spectrometer signal for each sample a characteristic response indicative of the concentration of the second target analyte in each sample; and comparing the characteristic response of the second target analyte in each sample to the second calibration curve to quantify the second target analyte in each sample.

In various aspects, each characteristic response may comprise a cumulative intensity of the mass spectrometer signal. In some implementations, the mass spectrometer signal exhibits an intensity for each m/z, and wherein each characteristic response comprises a separate intensity peak of the mass spectrometer signal for at least one unique m/z corresponding to each of the plurality of calibrants. In some related aspects, the unique m/z corresponding to each of the plurality of calibrants comprises the m/z of a fragment ion for each of the plurality of calibrants.

Isotopic analogs in accordance with the present teachings can also be used as internal standards in the sample and/or inter-sample controls such as quality controls. For example, quality control solutions comprising known quantities of three isotopic analogs can be used to confirm instrument functioning between samples of a batch. In some aspects, the method can further comprise adding an internal standard to the calibration mixture and each of said series of samples prior to generating the mass spectrometer signal for each of the series of samples, wherein the internal standard comprises a third isotopic analog distinguishable by mass spectrometry from the standard of the target analyte, the first isotopic analog, and the second isotopic analog.

In some implementations, obtaining a mass spectrometer signal for the calibration mixture comprises ionizing the calibrants or derivatives thereof; separating the ionized calibrants or derivatives thereof based on their mass-to-charge ratios (m/z); and detecting the m/z-separated ionized calibrants or derivatives thereof, wherein each of the ionized calibrants or derivatives thereof exhibit a unique m/z ratio relative to the other of the ionized calibrants or derivatives thereof. In some implementations, obtaining a mass spectrometer signal for the calibration mixture comprises ionizing the calibrants or derivatives thereof within the calibration mixture; fragmenting each of the ionized calibrants or derivatives thereof; and detecting at least one fragment of each of the ionized calibrants or derivatives thereof, wherein each of the ionized calibrants or derivatives thereof exhibit at least one unique multiple reaction monitoring (MRM) transition relative to the other of said ionized calibrants or derivatives thereof.

Apparatus, kits, and computer readable medium to practice the present teachings are also provided herein. In certain aspects of the present teachings, a kit for quantifying a target analyte of interest in a series of samples by mass spectrometry is provided, the kit comprising a calibration mixture comprising: a known quantity of a standard of the target analyte; a known quantity of a first isotopic analog of said target analyte; a known quantity of a second isotopic analog of said target analyte; wherein the known quantity of the standard, the first isotopic analog, and the second isotopic analog are different from one another within the calibration mixture, and wherein the standard, the first isotopic analog, and the second isotopic analog are each distinguishable from one another by mass spectrometry. The kit also includes instructions for (i) obtaining a mass spectrometer signal for the calibration mixture and (ii) generating a calibration curve for the calibration mixture based on a characteristic response of each of the standard, the first isotopic analog, and the second isotopic analog identified from the mass spectrometer signal to generate a calibration curve for a series of samples containing or suspected of containing the target analyte. The kit may further comprise reagents, buffers, solvents, vials plates, internal standards and/or quality controls.

In some implementations, the kit's calibration mixture comprises at least a third isotopic analog of the target analyte, wherein the third isotopic analog is at a different, known concentration and is distinguishable by mass spectrometry from the standard, the first isotopic analog, and the second isotopic analog. Additionally or alternatively, the kit's calibration mixture comprises a set of second calibrants for a second target analyte, wherein the set of second calibrants comprises a standard of the second target analyte, a first isotopic analog of the second target analyte, and a second isotopic analog of the second target analyte, wherein said second calibrants are distinguishable by mass spectrometry from one another and have different, known concentrations from one another in said calibration mixture and wherein said second calibrants are distinguishable by mass spectrometry from said standard of the target analyte, the first isotopic analog of the target analyte, and the second isotopic analog of the target analyte.

In some embodiments, the calibration mixture further comprises an internal standard, wherein the internal standard is a third isotopic analog of the target analyte distinguishable by mass spectrometry from the standard, the first isotopic analog, and the second isotopic analog.

Also provided herein is computer readable medium comprising computer executable instructions when executed on a processor render the processor operative to obtain a mass spectrometer signal of a calibration mixture comprising a known quantity of a plurality of calibrants, wherein the plurality of calibrants comprise a standard of the target analyte, a first isotopic analog of the target analyte, and a second isotopic analog of the target analyte, wherein the plurality of calibrants are distinguishable by mass spectrometry from one another and have different, known concentrations from one another in said calibration mixture. The computer executable instructions are also operative to identify from the mass spectrometer signal for the calibration mixture a characteristic response of each of said plurality of calibrants, wherein each of the characteristic responses correspond to a different one of the plurality of calibrants and is indicative of the concentration of each of the plurality of calibrants in the calibration mixture; and generate a single calibration curve for the calibration mixture based on said characteristic responses of said plurality of calibrants.

In some embodiments, the computer executable instructions are further operative to obtain a mass spectrometer signal from each of a series of samples; identify from the mass spectrometer signal for each sample a characteristic response indicative of the concentration of the target analyte in each sample; and compare the characteristic response of the target analyte in each sample to the single calibration curve to quantify the target analyte in each sample.

Also provided herein is a method of verifying a calibration curve generated for a target analyte in a series of samples by mass spectrometry, the method comprising: generating a calibration curve for a target analyte that relates characteristic responses of a mass spectrometer signal to a quantity, obtaining a mass spectrometer signal for a quality control mixture, wherein the quality control mixture comprises a plurality of quality controls selected from the group comprising a standard of the target analyte, a first isotopic analog of the target analyte, and a second isotopic analog of the target analyte, wherein said plurality of quality controls are distinguishable by mass spectrometry from one another and have different, known concentrations from one another in said quality control mixture; identifying from the mass spectrometer signal for the quality control mixture a characteristic response of each of said plurality of quality controls, wherein each of the characteristic responses corresponds to a different one of the plurality of quality controls in the quality control mixture; comparing the characteristic responses of each of the plurality of quality controls to the calibration curve for the target analyte and determining a quantity from the calibration curve for each of the plurality of quality controls; and; comparing the determined quantity of each of the plurality of quality controls to the known concentrations.

In some embodiments, the method of verifying a calibration curve can further comprise identifying a fault condition when the determined quantity of each of the plurality of quality controls differs from the known concentrations by a predetermined threshold. In some embodiments, the predetermined threshold is a difference of 10%.

Also provided herein is a method of quantifying a target analyte in a series of samples by mass spectrometry, the method comprising: obtaining a mass spectrometer signal for a calibration mixture, wherein the calibration mixture comprises a plurality of calibrants selected from the group comprising a standard of the target analyte reacted with a first derivatizing agent, a target analyte reacted with a second derivatizing agent, and a target analyte reacted with a third derivatizing agent, the first, second and third derivatizing agents being isotopic analogues of one another and wherein said plurality of calibrants are distinguishable by mass spectrometry from one another and have different, known concentrations from one another in said calibration mixture; identifying from the mass spectrometer signal for the calibration mixture a characteristic response of each of said plurality of calibrants, wherein each of the characteristic responses corresponds to a different one of the plurality of calibrants and the mass spectrometer signal is indicative of the concentration of each of the plurality of calibrants in the calibration mixture; generating a single calibration curve for the calibration mixture based on said characteristic responses of said plurality of calibrants; creating a derivatized sample for each of the series of samples by reacting each of the series of samples with the first derivatizing agent, the second derivatizing agent, the third derivatizing agent or an isotopic analog thereof, obtaining a mass spectrometer signal from each of the derivatized samples from the series of samples; identifying from the mass spectrometer signal for each of the derivatized samples from the series of samples a characteristic response indicative of the concentration of the target analyte in each derivatized sample; and comparing the characteristic response of each of the derivatized samples in the series of samples to the single calibration curve to quantify the target analyte in each sample.

Also provided herein is a method of quantifying an analyte in a series of samples by mass spectrometry, the method comprising: obtaining a mass spectrometer signal for a calibration mixture, wherein the calibration mixture comprises a plurality of calibrants, wherein each of the plurality of calibrants comprises a first compound, a first isotopic analog of the first compound or a second isotopic analog of the first compound, wherein each of the first compound and first and second isotopic analogs of the first compound are distinguishable by mass spectrometry from one another and have different, known concentrations from one another is said calibration mixture, identifying from the mass spectrometer signal for the calibration mixture a characteristic response of each of said plurality of calibrants, wherein each of the characteristic responses corresponds to a different one of the plurality of calibrants and the mass spectrometer signal is indicative of the concentration of each of the plurality of calibrants in the calibration mixture; generating a single calibration curve for the calibration mixture based on said characteristic responses of said plurality of calibrants; obtaining a mass spectrometer signal from each of a series of samples, each of the series of samples containing a target analyte having the same structure as the first compound or an isotopic analog of the first compound; identifying from the mass spectrometer signal for each sample a characteristic response indicative of the concentration of the target analyte in each sample; and comparing the characteristic response of the target analyte in each sample to the single calibration curve to quantify the target analyte in each sample.

In some embodiments, each of the plurality of calibrants comprises a reaction product of a molecule that is being tested for and a derivatizing agent and wherein each of the derivatizing agents utilized for each of the plurality of calibrants is an isotopic analog of the other derivatizing agents. In some embodiments, the molecule that is being tested for is a peptide or a hormone. In some embodiments, the molecule is testosterone.

In some embodiments, the compound is a peptide or a hormone. In some embodiments, the hormone is testosterone.

These and other features of the applicant's teaching are set forth herein.

BRIEF DESCRIPTION OF THE DRAWINGS

The foregoing and other objects and advantages of the invention will be appreciated more fully from the following further description, with reference to the accompanying drawings. The skilled person in the art will understand that the drawings, described below, are for illustration purposes only. The drawings are not intended to limit the scope of the applicant's teachings in any way.

FIG. 10 depicts exemplary calibrants along with their concentrations for generating a calibration curve and quantifying the peptides VIFDANAPVAVR and FSPDDSAGASALLR in accordance with various aspects of the present teachings.

FIG. 13 depicts an embodiment of a workflow for measuring thyroglobulin.

FIG. 17 identifies various permutations that can be utilized to create mass distinguishable derivatized analytes (i.e., combination and surrogate analytes).

DETAILED DESCRIPTION

Figure 1:
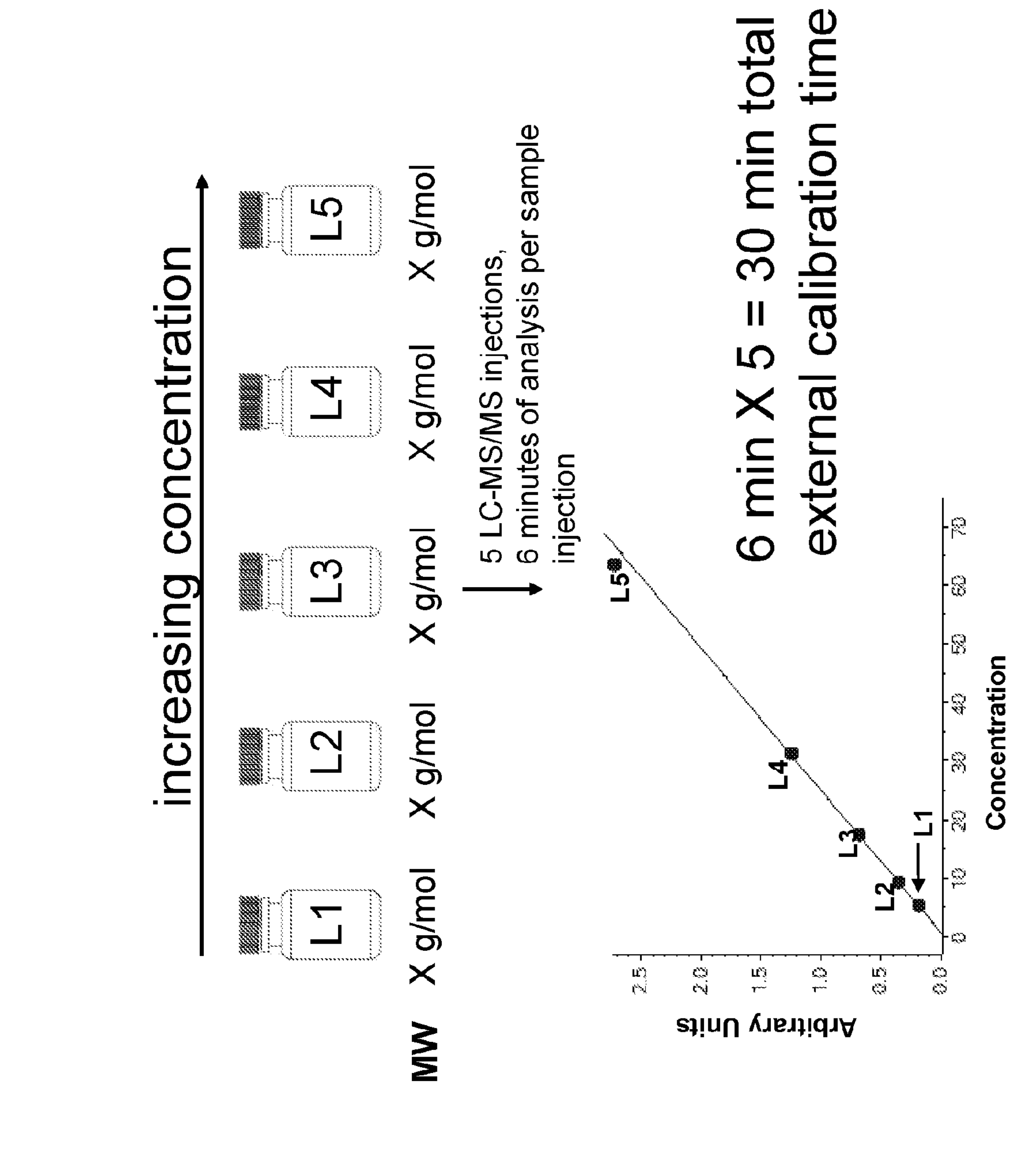
FIG. 1 schematically depicts a conventional external calibration process.

It will be appreciated that for clarity, the following discussion will explicate various aspects of embodiments of the applicant's teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicant's teachings may not require certain of the specifically described details in every implementation, which are set forth herein only to provide a thorough understanding of the embodiments. Similarly, it will be apparent that the described embodiments may be susceptible to alteration or variation according to common general knowledge without departing from the scope of the disclosure. The following detailed description of embodiments is not to be regarded as limiting the scope of the applicant's teachings in any manner. As used herein, the terms "about" and "substantially equal" refer to variations in a numerical quantity that can occur, for example, through measuring or handling procedures in the real world; through inadvertent error in these procedures; through differences in the manufacture, source, or purity of compositions or reagents; and the like. Typically, the terms "about" and "substantially" as used herein means greater or lesser than the value or range of values stated by 1/10 of the stated values, e.g., ±10%. For instance, a concentration value of about 30% or substantially equal to 30% can mean a concentration between 27% and 33%. The terms also refer to variations that would be recognized by one skilled in the art as being equivalent so long as such variations do not encompass known values practiced by the prior art.

Methods, compositions, kits, and apparatuses for MS-based quantification of a target analyte in a sample are provided herein for increasing the productivity and/or throughput of samples by reducing the time and/or cost associated with conventional techniques for external calibration.

In various embodiments, the present teachings enable a calibration mixture containing a plurality of calibrants to be analyzed in a single external calibration run (e.g., prior to analyzing a batch of samples), thereby reducing total analysis batch processing time by the time taken for separate analytical runs of the calibrants. In various aspects, calibration mixtures are provided containing different, known quantities of a plurality of calibrants selected from the group of a standard of the target analyte and/or stable isotopic analog(s) thereof, with each of the calibrants in the calibration mixture being distinguishable from one another by mass spectrometry such that a complete calibration curve can be generated from a single external calibration run. In various aspects, the plurality of calibrants may be distinguished from each other by a mass spectrometer due to differences in their mass (i.e., a difference in mass that can be resolved by a MS instrument), fragmentation pattern, or combinations thereof resulting from the presence of and/or location of different isotopes within various portions of the calibrants. Moreover, in some embodiments, the exemplary isotopic analogs described herein may be used as internal standards within the calibration mixture and the samples themselves so as to account for matrix effects and/or sample losses during sample preparation. Additionally or alternatively, control solutions including quality control solutions can utilize the exemplary isotopic analogs (e.g., three calibrators can be used as inter-sample controls) to validate instrument calibration over the course of the batch of samples.

In various embodiments, the calibration mixtures are provided containing different, known quantities of a plurality of calibrants wherein each of the plurality of calibrants comprises a first compound, a first isotopic analog of the first compound or a second isotopic analog of the first compound, wherein each of the first compound and first and second isotopic analogs of the first compound are distinguishable by mass spectrometry from one another and have different, known concentrations from one another is said calibration mixture. In some embodiments, the first compound may be an analytical target (e.g. a molecule that is being tested for such as for example testosterone) and each of the first and second isotopic analogs are isotopic analogs of the analytical target (e.g. 2,3,4-$^{13}C_3$-testosterone and 16,16,17-$^{2}H_3$-testosterone). In other embodiments, the compound and the first and second isotopic analogs of the first compound may be a reaction product between an analytical target (e.g. testosterone) and different derivatizing agents (e.g., Amplifex reagent depicted in FIG. 5 and an isotopic analog thereof) and wherein the first and second isotopic analogs of the first compound differ in mass as a result of the isotopic variation of the derivatizing agents.

In certain aspects, when the first compound contains a ketone or carboxylic acid functional group (e.g. testosterone), the derivatizing agents can be selected from the group of:

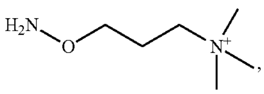
,
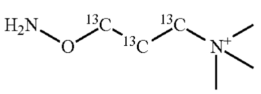

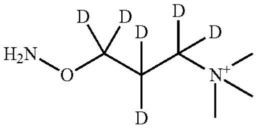

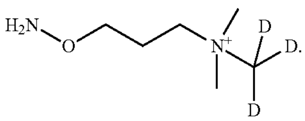
.

When such derivatizing agents are utilized with testosterone, the compound and its isotopic analogs can be one or more of the following compounds:

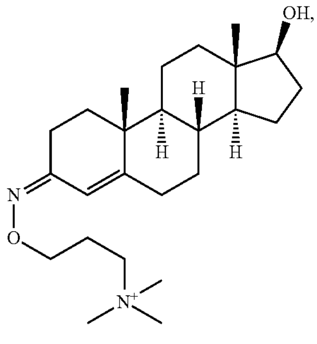
,

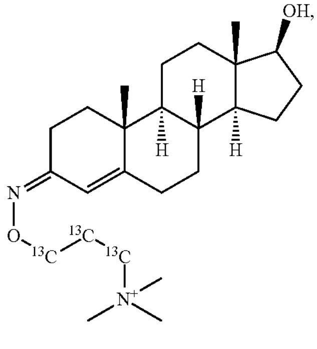
,

-continued

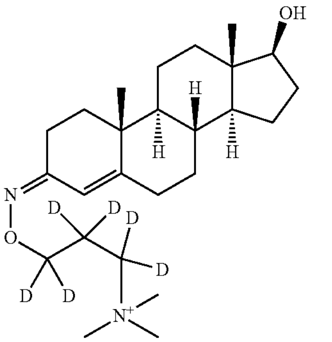

or

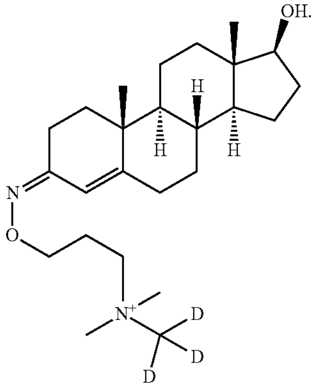

Such compounds can be incorporated into a kit.

A typical diagnostic quantitation workflow includes analyzing samples suspected of containing an unknown amount of one or more target analytes with a known amount (or a known amount pattern) of a standard of that analyte. Commonly, external calibration is first utilized to establish a relationship between the analytical signal obtained from the particular analytical method used and a known quantity of the standard. FIG. 1 depicts such a conventional prior art external calibration method for a target analyte (L having a molar mass of X g/mol), in which various known concentrations of the standard are subjected to the same analytical method (e.g., LC-MS, LC-MS/MS) to be used for samples containing unknown concentrations of the target analyte. In the example of FIG. 1, the conventional external calibration method performs the analytical method on a series of five calibration solutions, each of which contains the standard of the target analyte at a different concentration (i.e., L1, L2, L3, L4, L5) from the other calibration solutions. After subjecting each calibration solution to liquid chromatography, ionization, and mass spectrometry according to the analysis protocol to be used on the samples, the chromatogram generated from the MS signal is analyzed to identify a characteristic indicative of the quantity of the concentration in each of the five calibration runs. The plot of FIG. 1 depicts this characteristic value for each calibration solution as arbitrary units, though a person skilled in the art will appreciate that exemplary characteristics identifiable based on a mass spectrometer signal include peak intensity at particular mass-to-charge ratios (m/z) of the precursor ions or its product ion fragments (as in tandem mass spectrometry), the peak area of the ionized precursor analyte or its product ions, and combinations thereof. As is known in the art, the mass spectrometry signal can be used to generate a calibration curve based on the value of the characteristic at the five different concentrations such that the corresponding characteristic of the mass spectrometer signal for subsequent samples subject to the same analytical process can be compared to the calibration curve to quantify the concentration in each sample. As shown in this example, separately analyzing each calibration solution takes approximately 6 minutes such that the total calibration time for the five calibration solutions is about 30 minutes. It will be appreciated that if only a single sample is to be run, the calibration time would take five times longer than the MS-based analysis of the sample itself and require the use of five different calibrator solutions in this example. Accordingly, the cost per sample can become inefficient or prohibitive.

However, in certain embodiments, methods, compositions, kits, and apparatuses for MS-based quantification in accordance with various aspects of the present teachings increase the productivity and/or throughput of samples by reducing the time and/or cost associated with conventional techniques for external instrument calibration. Whereas the external calibration protocol depicted in FIG. 1 requires sequentially running solutions containing different concentrations of the same standard of the target analyte through the same analytical process to be applied to the sample, the present teachings as exemplified in FIG. 2 can enable the generation of a calibration curve from a single run of an analytical process on a calibration mixture containing a plurality of calibrants, thereby reducing external calibration time by a factor of five relative to that of FIG. 1.

Figure 2:
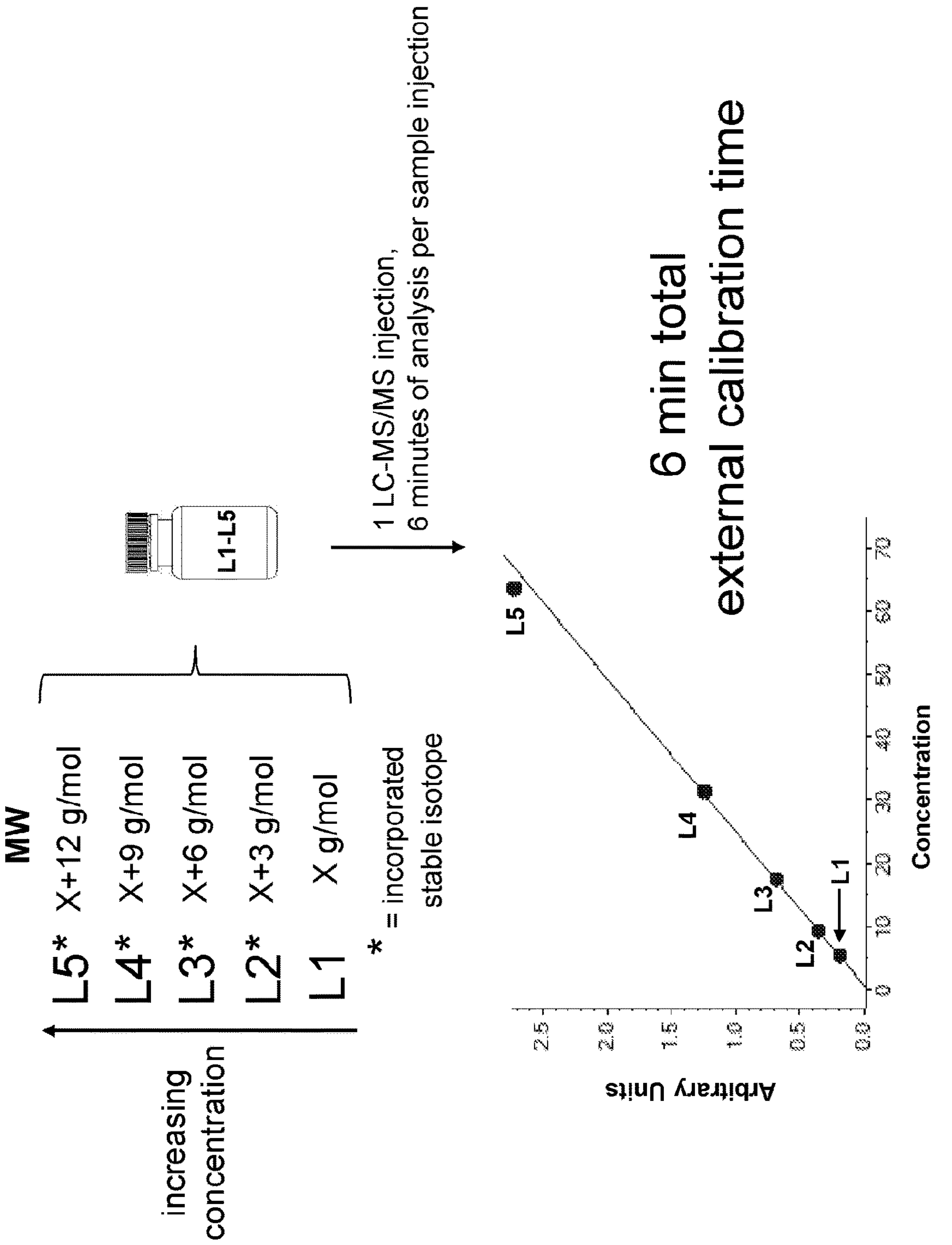
FIG. 2 schematically depicts an exemplary external calibration process according to various aspects of the present teachings.

FIG. 2 illustrates an embodiment of an exemplary calibration mixture in accordance with the present teachings. In the embodiment of FIG. 2, the calibration mixture comprises five external calibrants, each external calibrant being of known concentration different from the other external calibrants and distinguishable from the other external calibrants by mass spectrometry. In particular, the exemplary external calibration mixture comprises a concentration (L1) of the standard of the target analyte (L) and different concentrations of four different isotopic analogs of the target analyte (i.e., L2*, L3*, L4*, and L5*). While the example of FIG. 2 identifies the use of five external calibrants, other numbers of calibrants are contemplated as long as a sufficient number of analysis points are generated to cover the range of concentrations expected in the sample. Typically, embodiments will include at least three external calibrants, including the standard of the target analyte and two different isotopic analogs thereof, though certain implementations may find two calibrants (e.g., the standard and one isotopic analog, two isotopic analogs) will be sufficient or that higher numbers of external calibrants (e.g., 5, 6, 7, . . . ) may provide better resolution across an expected concentration range for the target analyte in the sample.

As discussed otherwise herein and will be appreciated by the skilled artisan, isotopes relate to nuclides with the same number of protons but differing numbers of neutrons (i.e., they have the same atomic number and are therefore the same chemical element). Typically, different isotopes of the same chemical element generally have essentially the same chemical characteristics and therefore behave essentially identically in chemical and/or biological systems. Therefore, isotopic analogs of a corresponding target analyte include compounds that are essentially identical to the target analyte in chemical composition and structure, with the exception that at least one atom of the target analyte has been replaced by a corresponding isotope of said atom (e.g., at least one $^{1}H$ is replaced with $^{2}H$). As such, the isotopic analogs comprise compounds which, with respect to chemical composition, structure, and physicochemical properties, are similar to the target analyte but are distinguishable from each other and the target analyte based on their behavior in the mass spectrometer. That is, the isotopic analogs can mimic a corresponding target analyte such that at least one of the physicochemical properties of the isotopic analogs can be substantially indistinguishable from the corresponding physicochemical property of the target analyte (e.g., during sample preparation prior to injection into the mass spectrometer system). For example, the external isotopic analog and its corresponding target analyte may be indistinguishable on the basis of one or more of solubility, retention time (e.g., in a separation technique such as LC), affinity (e.g., to an antibody specific for said target analyte), dissociation constant, reactivity, and/or specificity towards an enzyme (e.g., hydrolase, transferase). It will be appreciated that the preferred external isotopic analogs are generally absent or in a negligible amount in the sample to be analyzed. That is, the external isotopic analogs are generally compounds (including synthetic compounds) that do not naturally occur in the sample or exhibit a natural abundance in the sample that is below a threshold detection limit of a mass spectrometer. For example, the natural abundance of the isotope can be less than 49% (e.g., less than 40%, 30%, 20%, 10%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01% of the total amount of all existing isotopes). As such, in accordance with various aspects of the present teachings, one or more isotopic analogs of the target analyte differentiable by mass spectrometry from any calibrants in the calibration mixture and the target analyte may be used as an internal standard in the calibration mixture and the sample. In some additional or alternative embodiments, control solutions containing isotopic analogs of the target analyte may be utilized to validate instrument calibration over the course of the batch of samples (e.g., three isotopic analogs can be used as inter-sample controls).

Despite their physiochemical similarities, each of the plurality of the calibrants selected from the group of the standard and isotopic analogs in the calibration mixture is distinguishable by mass spectrometry relative to the other calibrants such that a complete calibration curve may be generated from a single external calibration run by identifying at least one unique characteristic response of each of the calibrants following MS. Such unique characteristics include situations where the external isotopic analogs and the standard of the target analyte can be distinguished from each other due to differences in their mass (e.g., a difference in m/z due to the presence of an isotope that can be resolved by a MS instrument), fragmentation pattern (e.g., via MRM), or combinations thereof (e.g., by monitoring unique MRM transitions). As will be appreciated by a skilled artisan based on the present teachings, such differences may result from the presence of different isotopes and/or the locations of these isotopes in the isotopic analogs. For example, the masses of the external isotopic analogs and the standard of the target analyte may each differ in at least one (or 2, 3, 4, 5, . . . ) mass unit such that the ionized species also exhibit differing and distinguishable m/z ratios when analyzed using mass spectrometry. By way of example, a first isotopic analog utilized as a calibrant includes one isotopic substitution relative to the standard, a second isotopic analog utilized as a calibrant includes two isotopic substitutions, a third isotopic analog utilized as a calibrant includes three substitutions, and so on. Additionally or alternatively, the location of the isotope within the isotopic analogs can differ such that upon fragmentation, unique product ions for each isotopic analog can be detected. Suitable isotopes include $^{2}H$ (deuterium, also referred to as D), $^{11}B$, $^{13}C$, $^{15}N$, $^{17}O$, $^{18}O$, $^{33}S$, $^{34}S$, $^{36}S$, $^{74}Se$, $^{76}Se$, $^{77}Se$, $^{78}Se$, and $^{82}Se$, all by way of non-limiting example. Many molecules that can be used as external calibrants in accordance with the present teachings are commercially available or can be prepared using known organic synthetic chemistry methods.

The calibration mixture typically comprises various, known concentrations of the calibrants so as to span the range of the expected concentration of the target analyte in the sample in order to facilitate quantification of the target analyte. For example, in accordance with various aspects of the present teachings, the calibration mixture comprises known concentrations that bracket the expected concentrations typically found in the batch of samples or may be prepared by combining a first known quantity of a first isotopic analog, a second known quantity of a second isotopic analog, and a third known quantity of the standard of the target analyte. In some aspects, for example, the amounts of the plurality of calibrants can be selected to provide accuracy and precision over a specific analytical range of an analyte (e.g., where a specific target analyte is known to vary within a predetermined window). In another example, the amounts of the isotopic calibrants in the calibration mixture is selected to provide maximum flexibility over the analytical range of the instrument (e.g., where a target analyte is expected to vary widely or multiple analytes having different properties are to be analyzed).

In various aspects, the concentration of the plurality of calibrants in the calibration mixture span a portion or essentially the entire analytical range of the target analyte in the sample to be analyzed, with the analytical range describing the range over which meaningful data can be collected (e.g., within pre-determined statistical parameters). For example, the analytical range may be defined by the detection limit of the calibrants or target analyte in a mass spectrometer and/or the expected amount(s) of target analyte in the sample. For example, the amount of one or more calibrants may be around the expected amount of the target analyte in the sample(s) (e.g., 50%, 95%, 100%, 105%, or 150% of the expected amount of the target analyte in the sample). If the amount of the target analyte in the sample is expected to vary by orders of magnitude, then the amount of one or more calibrants may be, for example, 1%, 10%, 100%, 1000%, or 10,000% of the expected amount of the target analyte in the sample. Additionally or alternatively, the amount of one or more of the calibrants may be around/above the lower end of the analytical range of the calibrants in the instrument (e.g., 95%, 100%, 105%, 1000%, or 10,000% of the lower end of the analytical range of the calibrants in the instrument). Similarly, the amount of one or more calibrants may be around/below the upper end of the analytical range of the calibrant in the instrument (e.g., 0.1%, 1%, 95%, 100%, or 105% of the upper end of the analytical range of the calibrant in the instrument). Moreover, the relative amounts of any two calibrants (e.g., the calibrants present in the highest and lowest amounts) may be defined by a ratio, for example: 2:1, 3:1, 4:1, 5:1, 6:1, 7:1, 8:1, 9:1, 10:1, 100:1, 1,000:1, 10,000:1, 100,000:1, 1,000,000:1, or more. The ratio between the amounts of calibrants may be linear (e.g., 2 times, 3 times, 4 times), exponential (e.g., $10^1$ times, $10^2$ times, $10^3$ times), random, or a combination or variation thereof. In certain embodiments, the concentration of the heaviest isotopic analog of the target analyte in the calibration mixture is less than the concentration of the other of said isotopic analogs in the calibration mixture. Additionally or alternatively, in some embodiments the concentration of the lightest isotopic analog of the target analyte in the calibration mixture is greater than the concentration of the other of said isotopic analogs in the calibration mixture. In such aspects, the skilled artisan will appreciate that the calibration mixture can increase the dynamic range of the instrument during calibration.

Compositions according to the present teachings can comprise dry preparations and liquid preparations (e.g., a solution, emulsion, suspension, etc.) of the calibrants. The compositions in accordance with some embodiments may also contain other reagents, consumables, and/or quality controls. Liquid preparations can include various inorganic or organic solvents, or mixtures thereof, which are compatible with the calibrants, sample, and MS analysis. In some embodiments, the solvent is selected for compatibility with a preparation, extraction, or separation (e.g., a chromatographic mobile phase and media). Example solvents include water, acetonitrile, aliphatic alcohols (e.g., methanol, ethanol, propanol, iso-propanol), hexafluoroacetone, and combinations thereof. The solvent can include additives, such as buffer salts (e.g., ammonium acetate), inorganic or organic acids (e.g., formic acid, trifluoroacetic acid, orthophosphoric acid, heptafluorobutyric acid), and/or inorganic or organic bases (e.g., $NH_3$). Dry preparations include preparations that are substantially free from a liquid, for example a solvent (e.g., water) and may be prepared by various conventional drying techniques, such as air drying, vacuum drying, spray-drying, drum drying, dielectric drying, freeze drying (e.g., lyophilization), supercritical drying, or a combination thereof. Additionally, compositions in accordance with some embodiments of the invention include one or more additional substances, e.g., substances which improve the stability of the composition, improve or facilitate the processing of a sample, and/or allow, improve or facilitate the analysis of the target analyte(s). Moreover, the compositions may be contained in ready-to-use reaction tubes, for example, pre-aliquoted reaction tubes that can be directly used for analytical processing or analysis. Pre-aliquoted reaction tubes can contain calibrants in amounts and proportions sufficient for the analysis of one or more calibration mixtures. In some embodiments, the compositions may be part of a kit. The kit may also include reagents, buffers, solvents, vials plates, internal standards and/or quality controls.

In certain aspects, calibration mixtures in accordance with the present teachings can also include sets of calibrants for more than one target analyte, the calibrants for the second or more target analytes also being distinguishable from the other calibrants in the other set(s) by mass spectrometry. In such aspects, a single calibration run can therefore be utilized to generate calibration curves for multiple, different analytes in subsequently run samples (e.g., as for analytes in a common panel such as an opioid panel).

Figure 3:
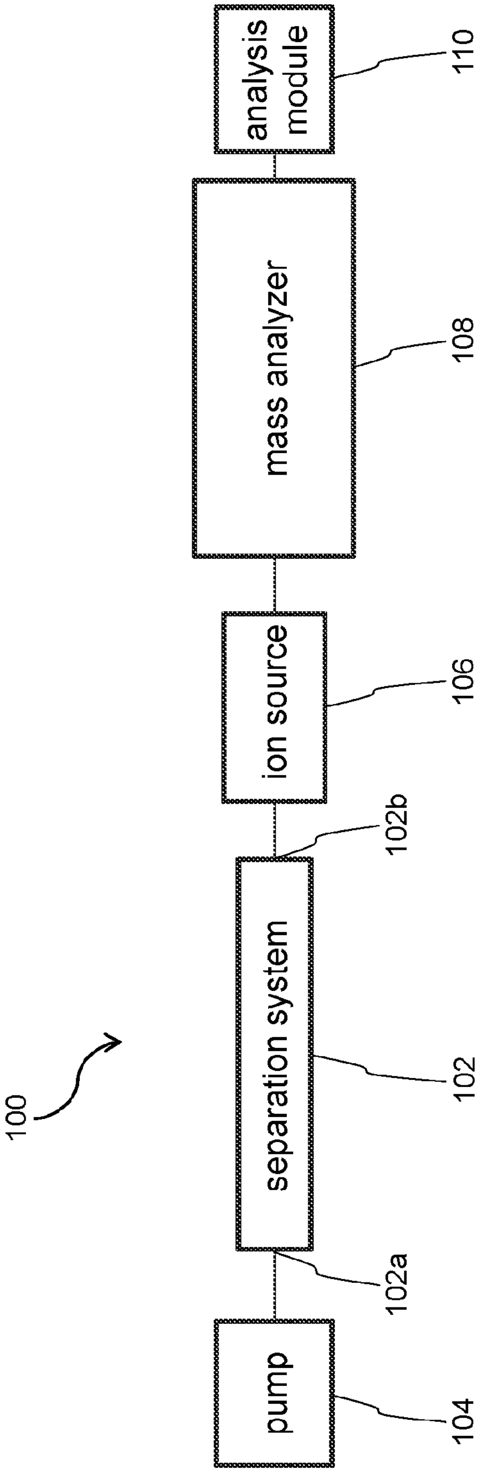
FIG. 3 depicts an exemplary system suitable for use in accordance with various aspects of the present teachings.

With reference now to FIG. 3, an exemplary system 100 according to various aspects of the present teachings is depicted. The system 100 includes a separation system 102 for separating the calibrants from the other components in a calibration mixture (and in a sample run to separate the target analyte and one or more internal standards from the other components in the sample). For example, the separation system 100 may comprise a liquid chromatography (LC) column. The exemplary system 100 further includes an ion source 106 disposed downstream of the LC column for ionizing at least a portion of the effluent exiting therefrom. A mass analyzer 108 receives the generated ions from the ion source 106 for mass analysis. As discussed in more detail below, in some embodiments, the mass analyzer 108 is a tandem mass analyzer (e.g., MS/MS) for cases where fragmentation may be used to distinguish between product ions. The system 100 further includes an analysis module 110 (herein also referred to as an analyzer) that can receive and analyze the data generated by the mass analyzer 108. In some embodiments, the analysis module 110 can be integrated in the mass spectrometer 100 while in other embodiments, for example, it can be implemented as a stand-alone unit.

As noted above, the system 100 includes a separation system 102 that separates the target analyte and calibrants from the other components in the calibration mixture or in a sample). Exemplary separation techniques include solid phase extraction (SPE), liquid-liquid extraction, precipitation, chromatography, (e.g., LC, HPLC), affinity, immunoaffinity, capillary electrophoresis and the like, all by way of non-limiting example. Separation system 102 can additionally provide various pre-treatment steps to prepare the sample for mass spectrometric analysis, including utilizing techniques such as derivatization. As shown, the separation system 102 includes an in-line LC column having an input port 102*a* for receiving a calibration mixture or sample and an output port 102*b* through which fluid output (effluent) exits the separation system 102. A pump 104 (e.g., an HPLC pump) drives a mobile phase and a calibration mixture into the LC column 102 via its input port 102*a*. It will be appreciated, however, that a pre-treatment/separation system suitable for use in accordance with the present teachings can operate in an off-line or on-line mode. In in-line LC-MS, the effluent exiting the LC column can be continuously subjected to mass spectrometric analysis to generate an extracted ion chromatogram (XIC), which depict detected ion intensity (a measure of the number of detected ions, total ion intensity or of one or more particular analytes) as a function of retention time. As discussed otherwise herein, the LC effluents may alternatively be subjected to tandem mass spectrometry for identification of ions corresponding to the peaks in the XIC. For example, the precursor ions may be selected based on their m/z ratio to be subjected to subsequent stages of mass analysis. For example, the selected precursor ions may be fragmented (e.g., via collision induced dissociation), with the fragment ions (also referred to as product ions) being analyzed via a subsequent stage of mass spectrometry.

It will also be appreciated that the ion source 106 for ionizing at least a portion of the calibration mixture or sample may have a variety of configurations as is known in the art. Indeed, the ion source 106 may be any known or hereafter developed ion source for generating ions. Non-limiting examples of ion sources suitable for use with the present teachings include atmospheric pressure chemical ionization (APCI) sources, electrospray ionization (ESI) sources, continuous ion source, a glow discharge ion source, a chemical ionization source, or a photo-ionization ion source, among others.

Moreover, a variety of mass analyzers may be utilized for the practice of the present teachings. By way of example, the mass analyzer 108 depicted in FIG. 3 may generally comprise a mass spectrometer system such as a QTRAP® Q-q-Q hybrid linear ion trap mass spectrometer, as generally described in an article entitled "Product ion scanning using a Q-q-$Q_{linear}$ ion trap (Q TRAP®) mass spectrometer," authored by James W. Hager and J. C. Yves Le Blanc and published in Rapid Communications in Mass Spectrometry (2003; 17: 1056-1064), which is hereby incorporated by reference in its entirety, and modified in accordance with various aspects of the present teachings. Other non-limiting, exemplary mass spectrometer systems that can be modified in accordance with the systems, devices, and methods disclosed herein can be found, for example, in U.S. Pat. No.

7,923,681, entitled "Collision Cell for Mass Spectrometer," which is hereby incorporated by reference in its entirety. Other configurations, including but not limited to those described herein and others known to those skilled in the art, may also be utilized in conjunction with the systems, devices, and methods disclosed herein. For example, it will be appreciated that the one or more mass analyzers can be any of triple quadrupoles, linear ion traps, quadrupole time of flights, Orbitrap or other Fourier transform mass spectrometers, all by way of non-limiting example. As will be appreciated by a person of skill in the art, in a triple quadrupole configuration, a first quadrupole rod set Q1 may be operated as a conventional transmission RF/DC quadrupole mass filter to select an ion of interest and/or a range of ions of interest. For example, by taking the physical and electrical properties of Q1 into account, parameters for an applied RF and DC voltage may be selected so that Q1 establishes a transmission window of chosen m/z ratios, such that these ions traverse Q1 largely unperturbed. Ions having m/z ratios falling outside the window, however, do not attain stable trajectories within the quadrupole and can be prevented from traversing the quadrupole rod set Q1. It should be appreciated that this mode of operation is but one possible mode of operation for Q1. By way of example, a lens between Q1 and Q2 can be maintained at a higher offset potential than Q1 such that the quadrupole rod set Q1 be operated as an ion trap. In some aspects, the ions can be Mass-Selective-Axially Ejected from the Q1 ion trap in a manner described by Hager in "*A new Linear ion trap mass spectrometer*," Rapid Commun. Mass Spectro. 2002; 16: 512-526, and accelerated into Q2, which allow the ions to be passed therethrough, trap the ions, or operate as a collision cell, for example. A suitable collision gas (e.g., nitrogen, argon, helium, etc.) may be provided by way of a gas inlet (not shown) to thermalize and/or fragment ions in the ion beam. Ions transmitted by Q2 can pass into an adjacent quadrupole rod set Q3, which can also be operated in a number of manners, for example as a scanning RF/DC quadrupole or as a linear ion trap. Following processing or transmission through Q3, the ions are transmitted into a detector operated in a manner known to those skilled in the art in view of the systems, devices, and methods described herein to generate a mass spectrometer signal. As will be appreciated by a person skill in the art, any known detector, modified in accord with the teachings herein, can be used to generate and detect the ions.

Though the teachings herein are generally described in the context of a diagnostic assay for clinical chemistry, the present teachings should not be so limited. Rather, the utilization of external calibration and the combination of LC or other separation techniques and MS or MS/MS is an important analytical tool for identification and quantification of compounds within a wide variety of samples including in the fields of medicine, veterinary medicine, chemistry, pharmacology, environmental pollution monitoring, and food safety, all by way of non-limiting example.

Figure 4:
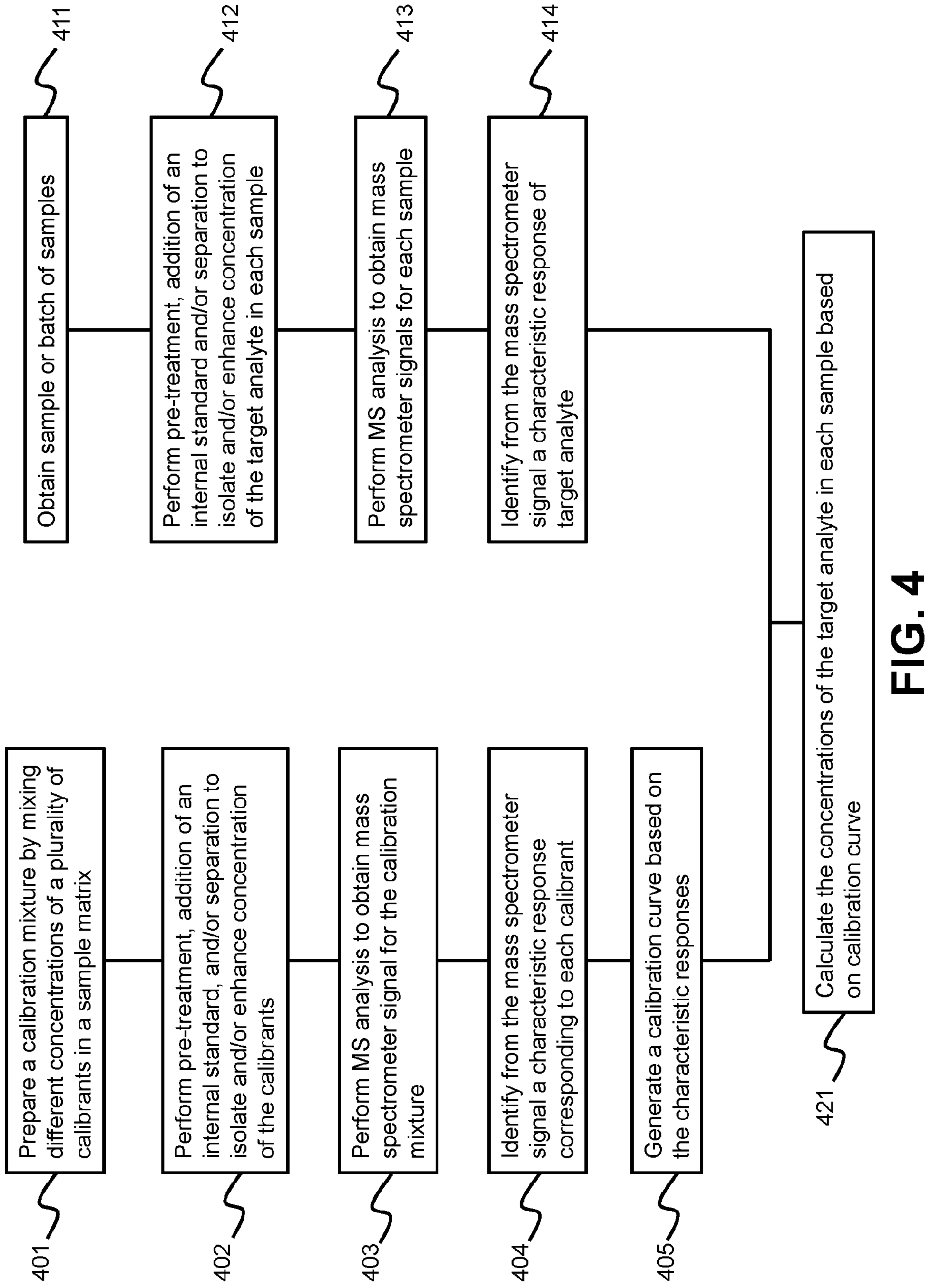
FIG. 4 depicts a flow chart of an exemplary method for quantifying a target analyte according to various aspects of the present teachings.

FIG. 4 presents a flow chart outlining an example method for quantifying a target analyte in one or more samples based on a calibration curve generated from a single external calibration run in accordance with various aspects of the present teachings as discussed otherwise herein. As shown, step 401 comprises preparing an external calibration mixture, for example, by mixing different concentrations of a plurality of calibrants selected from the group comprising a standard of the target analyte of interest and isotopic analogs of the target analyte to result in known, differing concentrations in the calibration mixture. In accordance with the present teachings, it will be appreciated that selected calibrants can be obtained from commercial sources or by custom synthesis. Further, for stable isotopic calibrants, synthesis can provide appropriate isotopic labels in the appropriate parts of the molecules. Synthesis can provide one or more desired properties permitting the target analyte and isotopic analogs to be distinguished from each other and their responses independently measured using mass spectrometry.

In some aspects, the calibration mixture can be subject to MS analysis directly (step 403), though in some embodiments, the calibration mixture can first be added for example to a blank sample or surrogate matrix to replicate one or more conditions of the sample to be tested. Depending upon the makeup of the sample of interest, suitable matrices include a bodily fluid (e.g., serum, urine), a biopsy, an environmental sample, a food sample, all by way of non-limiting example. A person skilled in the art will also appreciate that a surrogate matrix similar in composition to the sample matrix can be used during external calibration in order to account for some matrix effects such as interference by some compounds in the naturally-occurring matrix. A suitable example of a human serum surrogate matrix, for instance, is a mixture containing bovine serum albumin (BSA).

According to the testing protocol to be applied to the sample in steps 412 and 413, the calibration mixture is subjected to pre-treatment or separation to isolate and/or improve the detectability (e.g., via derivatization) of calibrants within the calibration mixture in step 402. Such processing can be performed by techniques commonly used for processing samples prior to MS analysis, or by a combination of such techniques, in order to (1) reduce the number of compounds introduced into the mass spectrometer; (2) concentrate the calibrants or target analyte(s), e.g., by depleting unwanted compounds and/or enrichment of the calibrants or the target analyte; (3) separate the calibrants or target analyte(s) from other compounds that could interfere with the MS analysis; and/or (4) separate at least one set of calibrants or corresponding target analyte from other sets of calibrants or corresponding target analytes. Such techniques can include one or more of solid phase extraction, liquid phase extraction, and chromatography. It will also be appreciated that step 402 can, in some aspects, additionally or alternatively include adding an isotopic analog or another compound suitable for use as an internal standard in the sample runs discussed below to provide a baseline for validating instrument calibration over the course of the batch of samples, account for matrix effects and/or sample losses during sample preparation.

In step 403, analytes from the calibration mixture are then be subject to ionization and analysis in the mass spectrometer system, which may include one or more stages of mass analysis. Exemplary techniques result in the generation of a mass spectrometer signal corresponding to the quantity of parent ions (e.g., via MS), product ions, (e.g., via MS/MS), or both, for example, by monitoring m/z transitions following fragmentation of selected precursor ions. Such procedures may include loading a mixture containing one or more compounds onto the MS instrument and vaporizing the one or more compounds; ionizing the components of the mixture, to form charged particles (ions); separating the ions according to their m/z ratio in an analyzer using electric and/or magnetic fields; fragmenting the ions; and detecting the ions (e.g., by a quantitative method).

In step 404, at least one characteristic response for each calibrant may be identified from the mass spectrometer signal. For example, mass spectrometer signals typically exhibit an intensity for each m/z (or range of m/z) or at a certain time (e.g., depending on the timing of elution during LC), and the characteristic response for each calibrant may comprise a separate intensity peak at a unique m/z or time of the mass spectrometer signal, with the intensity of the mass spectrometer signal being correlated to the number of ions detected by the mass analyzer. Exemplary characteristics include peak intensity, peak area, and combinations thereof. It will also be appreciated that such procedures may include transforming the mass spectrometer signals into mass spectra for graphical display. For example, after separation and measurement of the intensities of the ions in the mass spectrometer, mass spectra may be created, for example by plotting the intensities measured for the detected ions vs. their m/z ratio. Depending on the mode by which the mass spectrometer is operated (full scan, selected ion monitoring (SIM), or MRM), the mass spectra can include (1) the peaks corresponding to all ions (precursor and product ions) detected in the mass spectrometer between two distant points on the m/z scale; (2) the peaks corresponding to (a) all ions which have a particular m/z value or which lie within a very small m/z range and optionally (b) all product ions derived from the ions specified under (a); or (3) only one or more selected product/daughter ions (MRM channels). For example, when the mass spectrometer is operated in MRM mode, a single mass spectrum may be created for a set of calibrants, with at least one unique peak for each calibrant. Alternatively, multiple mass spectra can be created for each calibrant. Mass spectra created using MRM channels and where peak intensities are plotted against time (such as retention time if the mass spectrometer is coupled to a SPE, chromatography, or electrophoresis device) are often described as mass chromatograms. Thus, the term mass spectra, as used herein, can also relate to mass chromatograms (e.g., where the MS operates in MRM mode). The MS signal intensities (or relative signal intensities) of the ions representative of each of the calibrants can be determined, for example, on the basis of the peak height or peak area (e.g., by integrating the signal intensity of a specific ion with respect to time). The intensities of the peaks in the mass spectrum/spectra can be normalized e.g., to 100%, to the most intense ion signal detected. As discussed above in the context of the properties and selection of calibrants, the isotopic calibrants and standard of the target analyte(s) can be distinguished from each other based on their behavior in a mass spectrometer (e.g., due to differences in their mass and/or fragmentation pattern).

In step 405, an external calibration curve may then be generated based on the characteristic responses of each calibrant, for example, by plotting the intensity of the mass spectrometer signal at a particular m/z against and the known concentration of the corresponding calibrants in the calibration mixture. Calibration curves may be obtained by applying a suitable regression algorithm (e.g., a Gauss least-square fitting method) to the data, for example. Suitable regression algorithms can include the following steps: (1) selecting a mathematical function (model); (2) fitting the function from the experimental data; and (3) validating the model. The function can be, but is not necessarily, linear over the entire analytical range. In embodiments in which the method is utilized to quantify multiple target analytes, the step of creating a calibration curve using the corresponding mass spectrometry signals can be performed for each set of external calibrants for a particular target analyte, thereby creating a distinct calibration curve for each target analyte.

With reference now to the right side of FIG. 4, the steps of which may occur before or after the external calibration protocol, the method comprises obtaining a sample or batch of samples containing or suspected of containing the target analyte of interest in step 411. In various embodiments, the sample(s) obtained may be directly injected into the MS system for analysis, though methods in accordance with the present teachings can alternatively include various pre-treatment processes known in the art to improve the detectability of the target analyte as shown in step 412. As noted above, exemplary techniques include one or more of solid phase extraction, liquid phase extraction, and chromatography in order to (1) reduce the number of compounds introduced into the mass spectrometer; (2) concentrate the target analyte(s), e.g., by depleting unwanted compounds and/or enrichment the target analyte; (3) separate the target analyte(s) from interfering compounds that could interfere with the MS analysis; and/or (4) separate at one type of target analyte from other types of target analytes. It will also be appreciated in accordance with some embodiments of the present teachings that step 412 can include adding an isotopic analog (distinguishable by mass spectrometry from the target analyte or the calibrants in the calibration mixture) or another compound suitable for use as an internal standard to the sample (preferably the same internal standard added to the calibration mixture in step 402) to validate instrument calibration over the course of the batch of samples, account for matrix effects, and/or sample losses during sample preparation.

In step 413, the sample(s) are then subjected to MS-based analysis, including ionizing the components of the mixture, to form charged particles (ions); separating the ions according to their m/z ratio in an analyzer using electric and/or magnetic fields; fragmenting the ions; and detecting the ions (e.g., by a quantitative method) ionization, separation by m/z, fragmentation, and detection as discussed above with reference to step 403.

In step 414, the mass spectrometer signal generated for each sample is then analyzed to identify at least one characteristic response unique to the target analyte(s) as discussed above with reference to step 404. By way of example, the characteristic response for each target analyte may comprise a peak intensity at a unique m/z of the mass spectrometer signal, with the intensity of the mass spectrometer signal being correlated to the number of target analyte ions detected by the mass analyzer.

In step 421, the external calibration curve may be utilized to determine the quantity of target analyte in the sample. For example, quantification may be achieved by extrapolation using the calibration curve for the calibrants and the characteristic response of the target analyte. When used to quantify multiple target analytes, each target analyte may be compared to its respective calibration curve.

In some embodiments, the external calibration mixture created in step 401 may be duplicated into a separate container and utilized as a quality control standard. In some embodiments, a quality control standard can be created that uses different concentrations of the isotopic analogs from those used in the external calibration mixture created in step 401. More specifically, such quality control standards may contain a number of different known concentrations of a plurality of isotopic analogs of a particular analyte, each distinguishable by mass spectrometry and the quality control standard utilized as one or more of the samples in the batch of samples in step 411. The quality control standard is processed through steps 412, 413, 414 and 421 and the mass spectrometer, calibration procedure, etc. calculates the quantity/concentration of one or more of the plurality of quality controls in the one or more of the samples. These values can then be compared to the actual known concentration of the plurality of quality controls to confirm that the calibration is correct and/or the analysis procedure is producing accurate results. If one of more of the calibrants is found to be outside of an acceptable limit when compared to the known value, for example if the difference is more than ±10%, or ±5%, appropriate steps can be taken such as repeating the calibration or modifying the procedure accordingly, or identifying a fault condition.

In various implementations, the method of FIG. 4 may be carried out manually, semi-automatically, or automatically. Similarly, one or more steps can be added, omitted, and/or repeated. The method of FIG. 4 (and its variants) can also serve as the basis for instructions (e.g., to be included in a kit, in human and/or machine readable format), for a program (e.g., an algorithm or computer program, embodied in a computer readable medium), and/or for analytical system (e.g., specifically adapted or purpose-built machine) for execution by a processor of a computing device to render the computing device operable to carry out the method steps. It will be appreciated that though analysis module 110 of FIG. 3 is depicted as a single component, one or more analysis units (whether local or remote) can be configured to execute a method according to the present teachings for quantifying a target analyte in a sample based on an external calibration. The analysis module 110 may take a hardware or software form, for example, the analysis module 110 may take the form of a suitably programmed computer, having a computer program stored therein that may be executed to implement methods according to the present teachings. Indeed, various software modules associated with the analysis module may execute programmable instructions to obtain mass spectrometer signals associated with the calibration mixture, generate a calibration curve therefrom, and analyze the sample mass spectrometer signals to identify at least one characteristic response that correlates with the concentration of the analyte of interest in the samples.

In alternative embodiments, the subject matter of the invention can be carried out by using derivatizing agents that can be distinguished using mass spectrometry. In specific embodiments, the derivatizing agents comprises two or more compounds that are isotopic variations of one another wherein one or more atoms in each of the variants is substituted with a heavier or lighter stable isotope. Though each of the derivatizing agents is distinguishable by mass, the variants are otherwise identical and have similar chemical and biochemical properties.

Each isotopic derivatizing agent can be used to derivatize an analyte (e.g. testosterone) to create a derivatized analyte wherein each derivatized analyte is distinguishable by mass spectrometry. Each derivatized analyte may then be mixed together in known quantities into a single container to make a calibrator mixture that can be utilized to generate calibration data. Examples of suitable derivatizing agents for testosterone (or other ketone or carboxylic acid containing analytes) include the Ampliflex Ketone reagent sold by Sciex where the reagent has been modified to include isotopic variants of the atoms contained therein. Other derivatizing agents that can be modified in accordance with the present teaching include the Ampliflex diene reagent.

In other embodiments, combinations of isotopic variants of the analyte and derivatizing with isotopic derivatizing agents may be used together to increase the possible calibrants that are distinguishable by mass spectrometry.

The applicant's teachings can be even more fully understood with reference to the following examples and data presented in FIGS. 5-17, which are provided to demonstrate but not limit the present teachings. As described below, an efficient external calibration protocol is provided for both hormones and peptides that utilizes a plurality calibrants including a standard and isotopic analogs to obtain a calibration curve based on a single MS run of the calibration mixture.

Example 1

Figure 5:
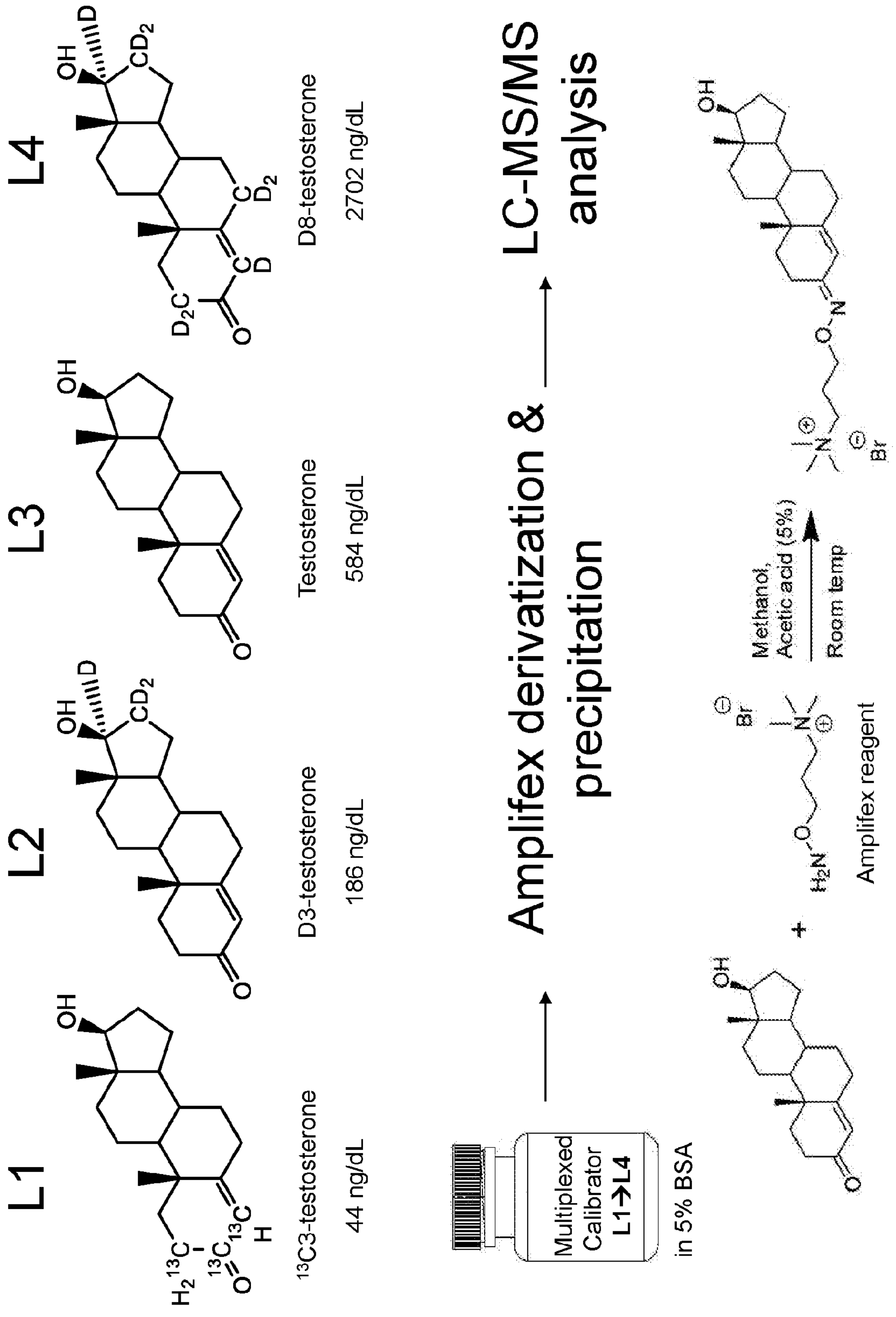
FIG. 5 depicts an exemplary calibration mixture for generating a calibration curve and quantifying testosterone in a sample according to various aspects of the present teachings.
Figure 6:
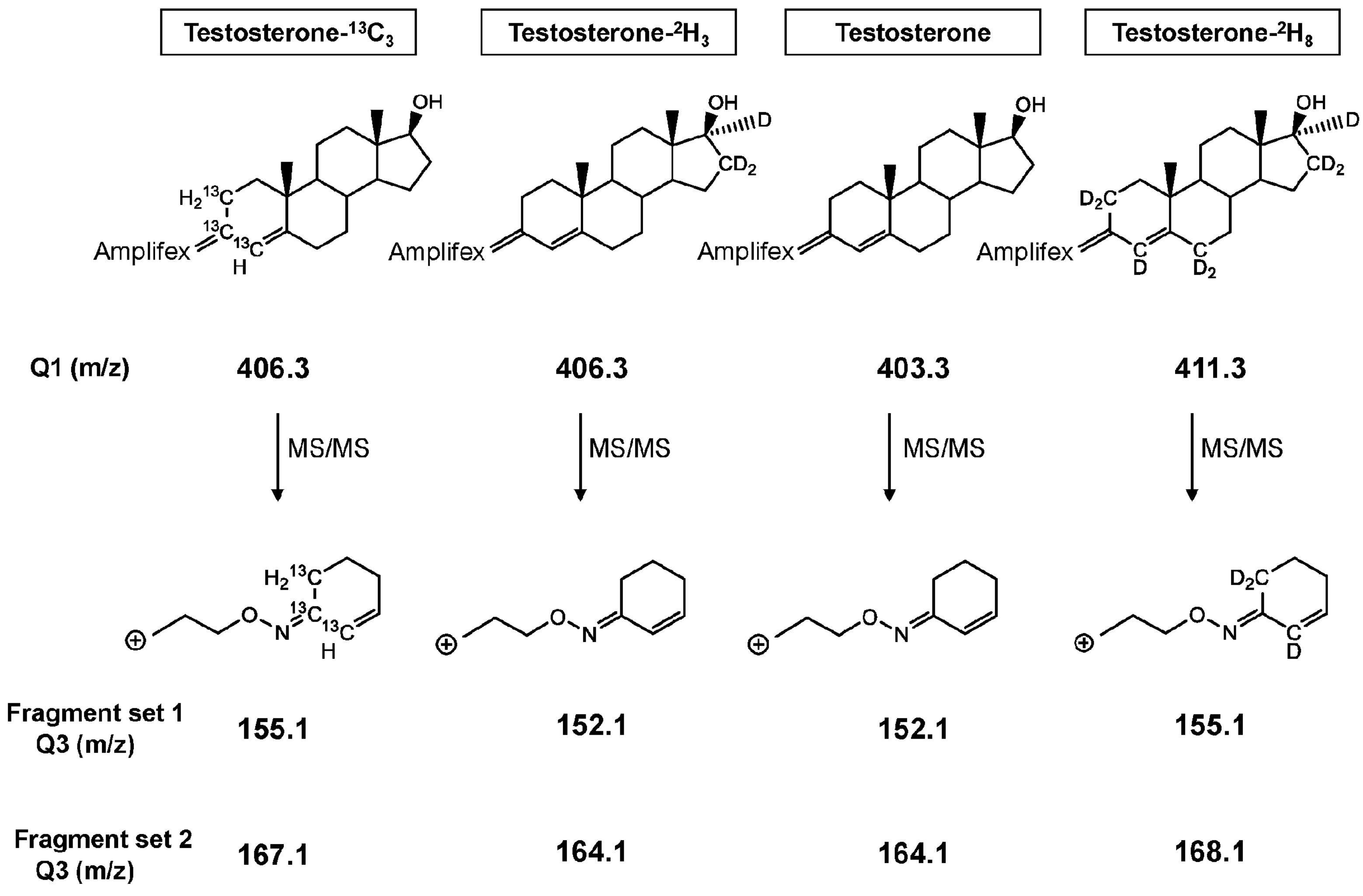
FIG. 6 depicts exemplary precursor and product ions of the calibration mixture of FIG. 5.
Figure 7:
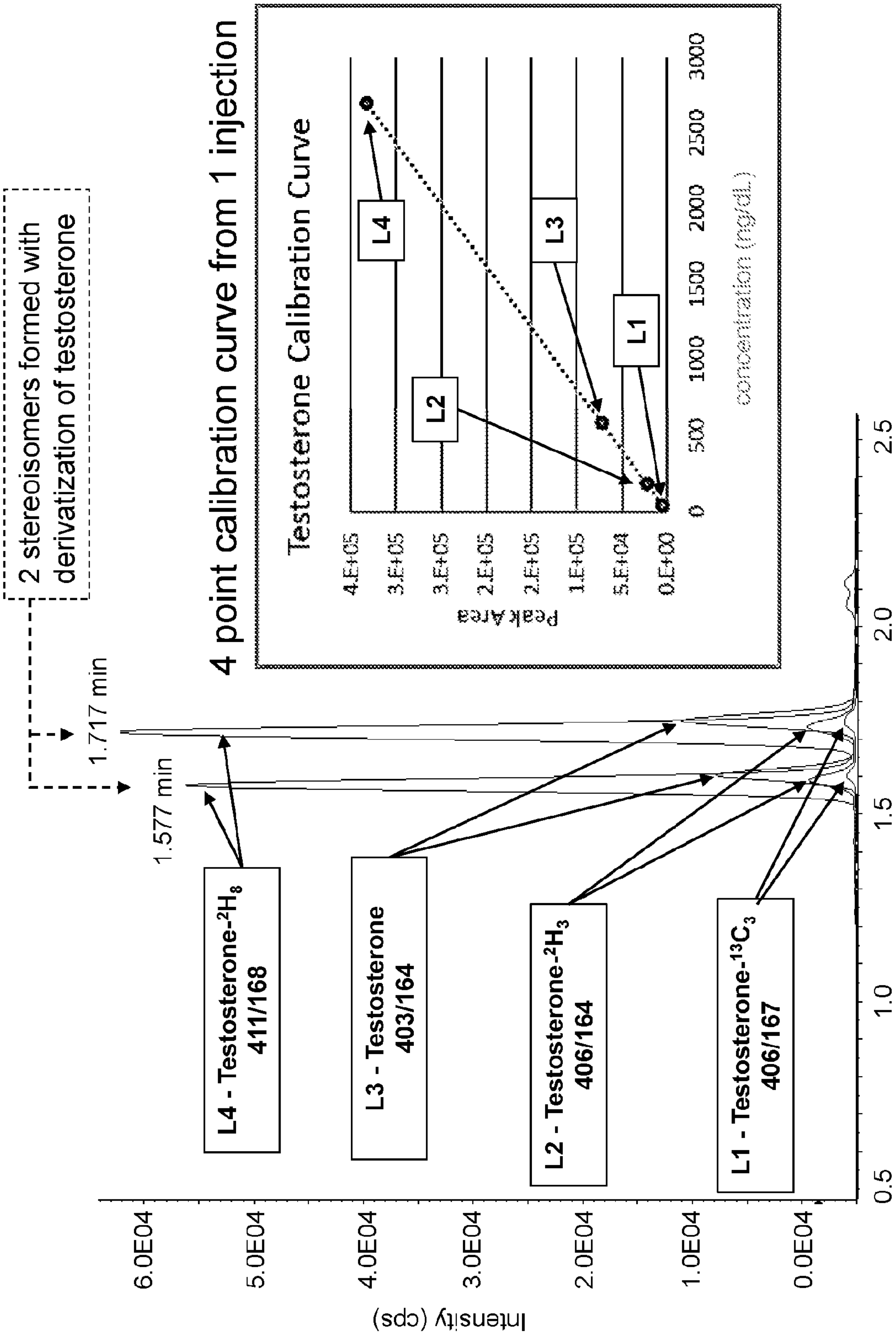
FIG. 7 depicts the XIC of the calibration mixture of FIG. 5 and the calibration curve generated therefrom as an example of embodiments of the present application.

With reference first to FIGS. 5-7, an exemplary protocol illustrates an embodiment for generating a calibration curve from a single calibration mixture for quantifying testosterone as the target analyte. As shown in FIG. 5, the calibration mixture comprises known concentrations of four calibrants: a standard of testosterone (584 ng/dL) and three isotopic analogs thereof in 5% bovine serum albumin (BSA). In particular, the calibration mixture comprises $^{13}$C3-testosterone at a concentration of 44 ng/dL, D3-testoserone at a concentration of 186 ng/dL, and D8-testosterone at a concentration of 2702 ng/dL. A known amount of the calibration mixture can then be precipitated and derivatized with the Amplifex Keto Reagent (marketed by SCIEX of Framingham, MA) in the presence of an added internal standard (IS) followed by LC-MS/MS analysis. LC separation of a 20 µL sample aliquot was accomplished on an Agilent 1290 HPLC system equipped with a Kinetex Biphenyl 50×3 mm ID LC column with particle size of 5 µm and 100 Å pore size from Phenomenex. Mobile phase A was water with 0.1% formic acid and mobile phase B was acetonitrile with 0.1% formic acid. The LC separation conditions were as follows: 90-70% A for 0-0.5 min, 70-60% A for 0.5-3.0 min, 60-5% A for 3.0-3.1 min, 5% A for 3.1-4.0 min, 5-90% A for 4.0-4.1 minutes and 90% A for 4.1-5 minutes. The eluent was subjected to electrospray ionization and tandem mass spectrometry using a SCIEX 5500 QTRAP tandem mass spectrometer. Derivatization with Amplifex Keto generates stereoisomers and the reported peak area for testosterone in a given sample is the sum for the two peak areas (peaks at 1.577 and 1.717 min in FIG. 7). As shown in FIG. 6, various precursor and product ions could be detected by the mass analyzer, with the m/z ratio of the ionized/derivatized testosterone analogs selected in Q1 as follows: $^{13}$C3-testosterone associated ion (m/z=406.3), D3-testoserone associated ion (m/z=406.3), standard testosterone associated ion (m/z=403.3), and D8-testosterone associated ion (m/z=411.3). Additionally, 8 product ions (fragment sets 1 and 2 in FIG. 6) resulting from the CID of each precursor ion could be detected as shown, with each of the calibrants exhibiting a unique precursor m/z, product m/z, and/or transition relative to the other of the calibrants. For example, with respect to the $^{13}$C3-testosterone associated ions and the D3-testoserone associated ions, each exhibited the same m/z for the precursor ion (m/z=406.3), but could be differentiated relative to one another based on the presence of unique product ions following dissociation. On the other hand, the D3-testoserone associated ions and standard testosterone associated ions each generated fragments of the same m/z (152.1, 164.1), but could be differentiated based on the m/z of the precursor ions. Thus, based on the exemplary calibrants of FIG. 6, for example, the external calibration protocol could utilize the unique MRM transitions of the three isotopic analogs and the target analyte standard to differentiate the MS signal for each compound in the calibration mixture. By way of example, the combination of the parent and fragment 2 m/z is unique to each of the different calibrants so as to enable detection of each independently via MS/MS. FIG. 7 depicts the XIC corresponding to fragment set 2 from FIG. 6 of the calibration mixture of FIG. 5 and the calibration curve generated therefrom. As shown, the calibration curve was generated based on the initial known concentration of each calibrant and the signal intensity of the mass spectrometer signal based on the particular characteristic response at these unique transitions. In accordance with the present teachings, one or more samples (e.g., spiked with one or more internal standards) having a similar characteristic response identified in the sample's mass spectrometer signal may subsequently be compared to the calibration curve of FIG. 7 so as to quantify the target analyte in the sample.

Example 2

Figure 8:
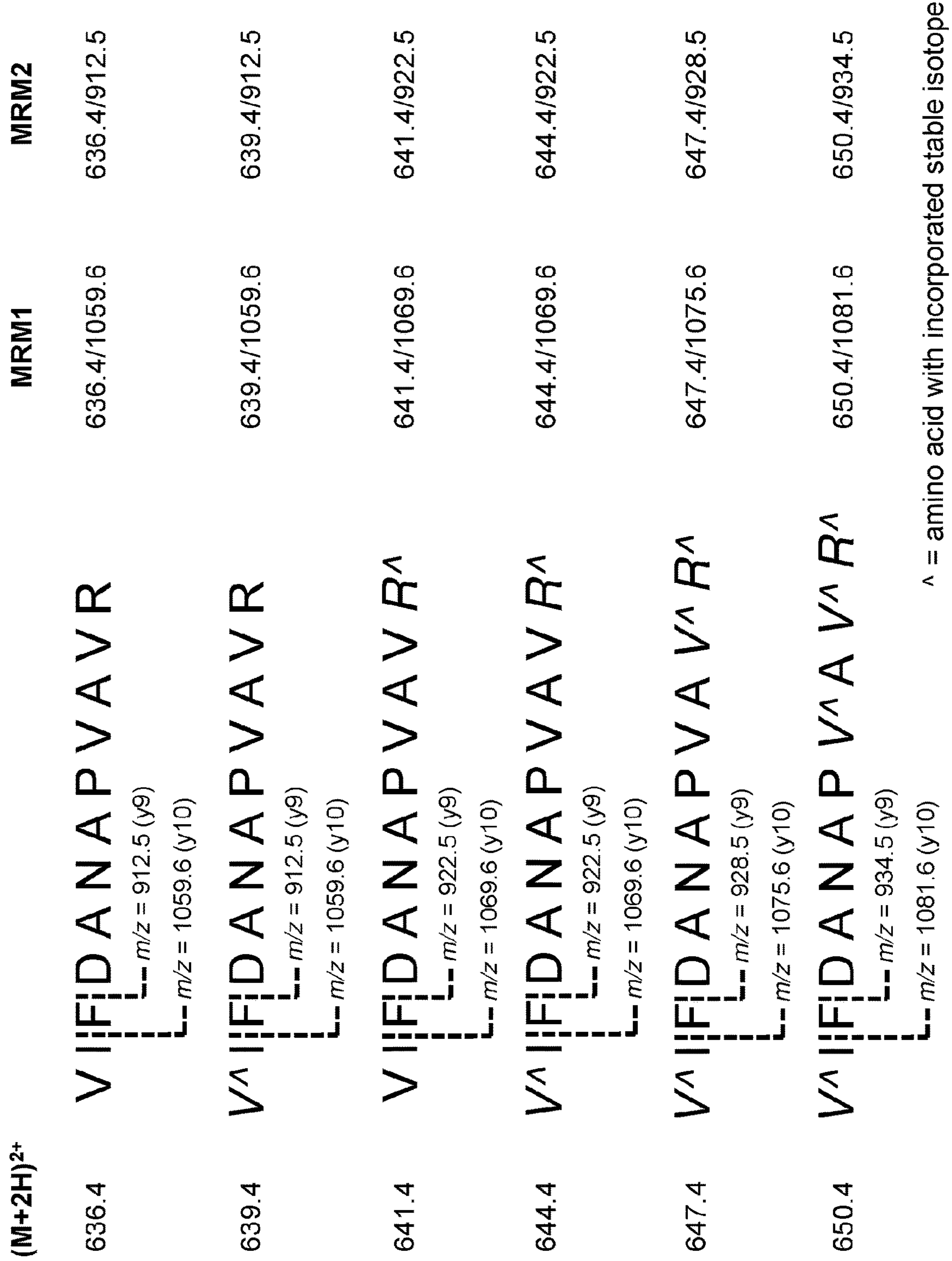
FIG. 8 depicts exemplary calibrants for generating a calibration curve and quantifying the peptide VIFDANAPVAVR in accordance with various aspects of the present teachings.
Figure 9:
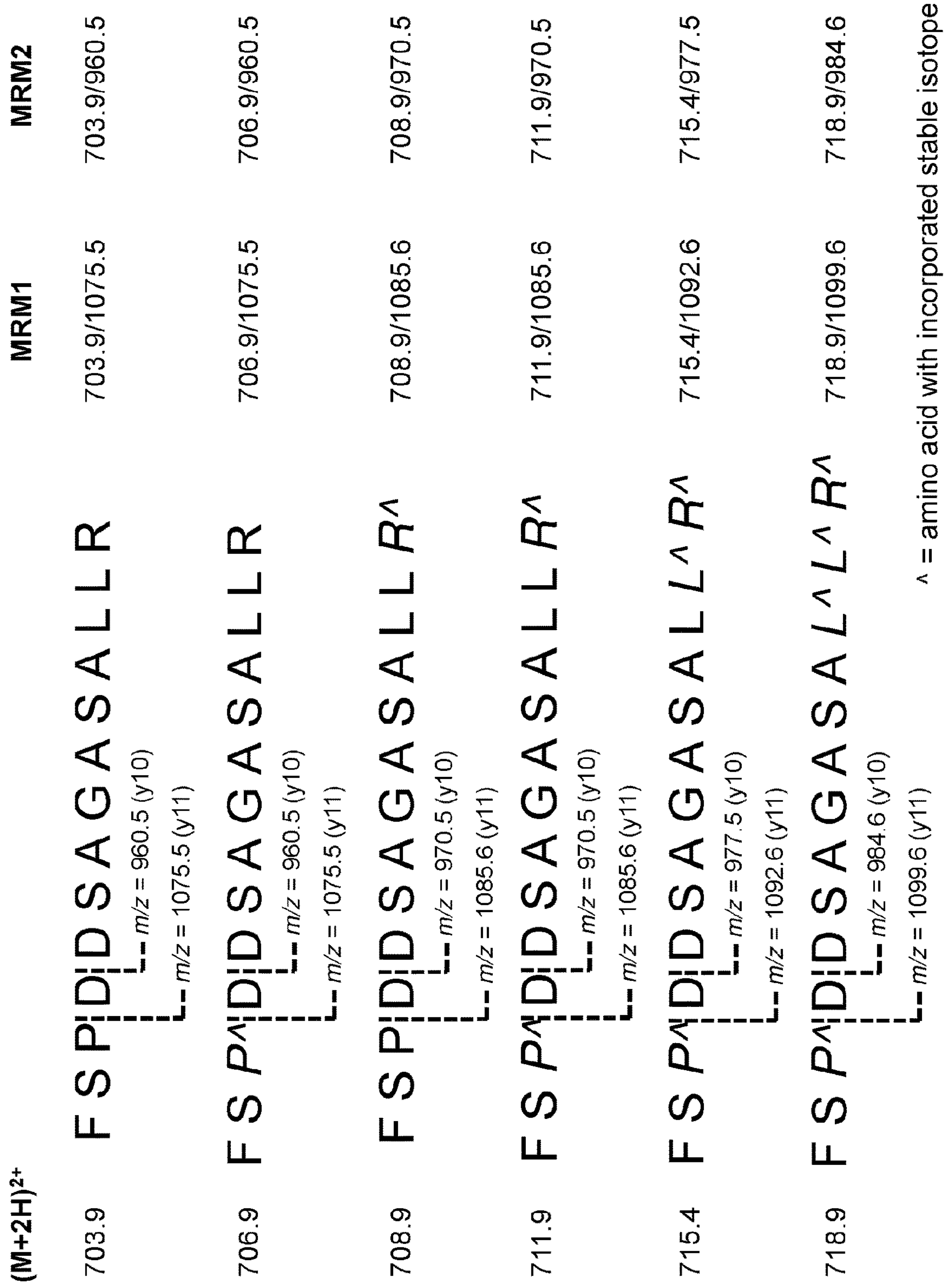
FIG. 9 depicts exemplary calibrants for generating a calibration curve and quantifying the peptide FSPDDSAGASALLR in accordance with various aspects of the present teachings.
Figure 11:
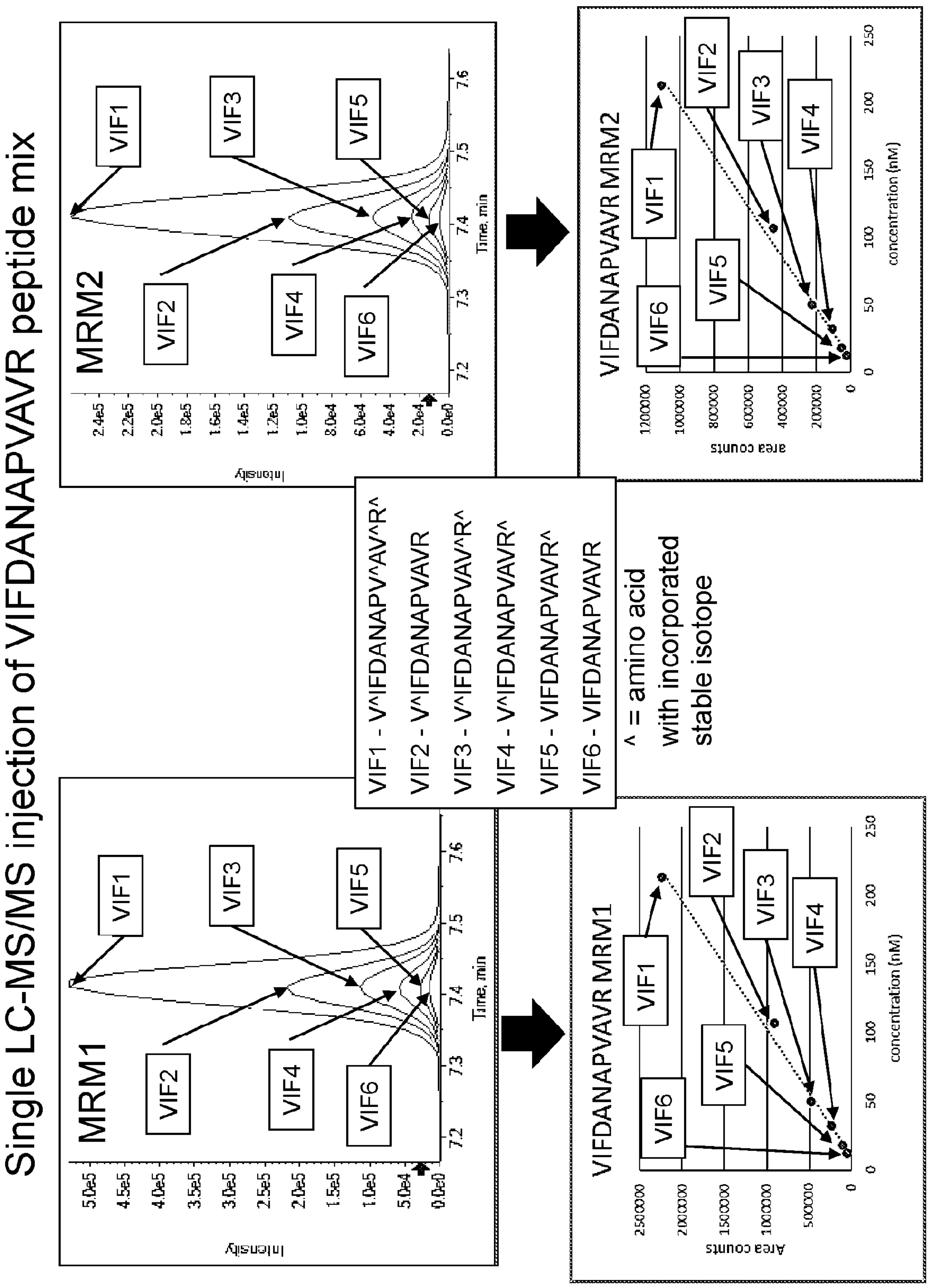
FIG. 11 depicts the XIC of the calibration mixture of FIG. 8 and the calibration curves generated therefrom for each peptide of VIFDANAPVAVR based on the characteristic response of MRM1 and MRM2 as an example of embodiments of the present application.

With reference now to FIGS. 8-13, an exemplary protocol for generating calibration curves from a single calibration mixture for quantifying two specific peptides as the target analytes is depicted. As shown in FIGS. 8 and 9, the particular peptide sequences VIFDANAPVAVR and FSPDDSAGASALLR can be used to quantify serum thyroglobulin, which is typically monitored in thyroid cancer patients following thyroidectomy and $^{131}$I ablation. In particular, FIG. 8 depicts a set of calibrants for the peptide VIFDANAPVAVR obtained by differentially labelling various amino acid positions (the ^ indicates that the amino acid has incorporated a stable isotope), as well as two common fragmentation patterns to result in the detectable MRM transitions shown in FIG. 11. For example, the isotopic analog V^IFDANAPVAVR was synthesized such that the terminal valine (V) contained isotopic carbon and nitrogen atoms while the VIFDANAPVAVR^ was synthesized such that the terminal arginine (R) contained isotopic carbon and nitrogen atoms. As shown in FIG. 8, the precursor ion associated with standard peptide VIFDANAPVAVR exhibits a m/z of 636.4 and fragments to form y10 product ions having an m/z of 1059.6 and y9 product ions having an m/z of 912.5. The precursor ion associated with the isotopic analog V^IFDANAPVAVR exhibits a m/z of 639.4 and fragments to form y10 product ions having an m/z of 1059.6 (MRM1=639.4/1059.6) and y9 product ions having an m/z of 912.5 (MRM2=639.4/912.5). The precursor ion associated with the isotopic analog VIFDANAPVAVR^ exhibits a m/z of 641.4 and fragments to form y10 product ions having an m/z of 1069.6 (MRM1=641.4/1069.6) and y9 product ions having an m/z of 922.5 (MRM2=641.4/922.5). The precursor ion associated with the isotopic analog V^IFDANAPVAVR^ exhibits a m/z of 644.4 and fragments to form y10 product ions having an m/z of 1069.6 (MRM1=644.4/1069.6) and y9 product ions having an m/z of 922.5 (MRM2=644.4/922.5). The precursor ion associated with the isotopic analog V^IFDANAPVAV^R^ exhibits a m/z of 647.4 and fragments to form y10 product ions having an m/z of 1075.6 (MRM1=647.4/1075.6) and y9 product ions having an m/z of 928.5 (MRM2=647.4/928.5). Finally, the precursor ion associated with the isotopic analog V^IFDANAPV^AV^R^ exhibits a m/z of 650.4 and fragments to form y10 product ions having an m/z of 1081.6 (MRM1=650.4/1081.6) and y9 product ions having an m/z of 934.5 (MRM2=650.4/934.5). It will thus be observed that the combination of the m/z of the precursor ion and fragment 1 is unique to each of the different calibrants so as to enable detection of each independently via MS/MS. Similarly, the combination of the m/z of the precursor ion and fragment 2 is unique to each of the different calibrants so as to also enable detection of each independently via MS/MS. As such, each of the MRM1 and MRM2 transitions represent characteristic responses for the six calibrants of the target VIFDANAPVAVR such that a calibration curve (FIG. 11) may be generated based on either the MRM1 or MRM2 transition by selecting a particular precursor ion in Q1 based on its m/z ratio, fragmenting the selected precursor ion in Q2, and monitoring the response at the respective m/z of each of the two common fragment ions of the selected precursor ion, with the intensity of the peak in the chromatograms of FIG. 12 being correlated with the known concentration of the VIFDANAPVAVR calibrants in the calibration mixture (FIG. 10). Accordingly, in accordance with the present teachings, the same MRM transitions monitored for the standard peptide VIFDANAPVAVR can be monitored while performing LC-MS/MS on a sample, with the resulting mass spectrometer signal compared to the calibration curves of FIG. 11 so as to quantify the target VIFDANAPVAVR in the sample.

Figure 12:
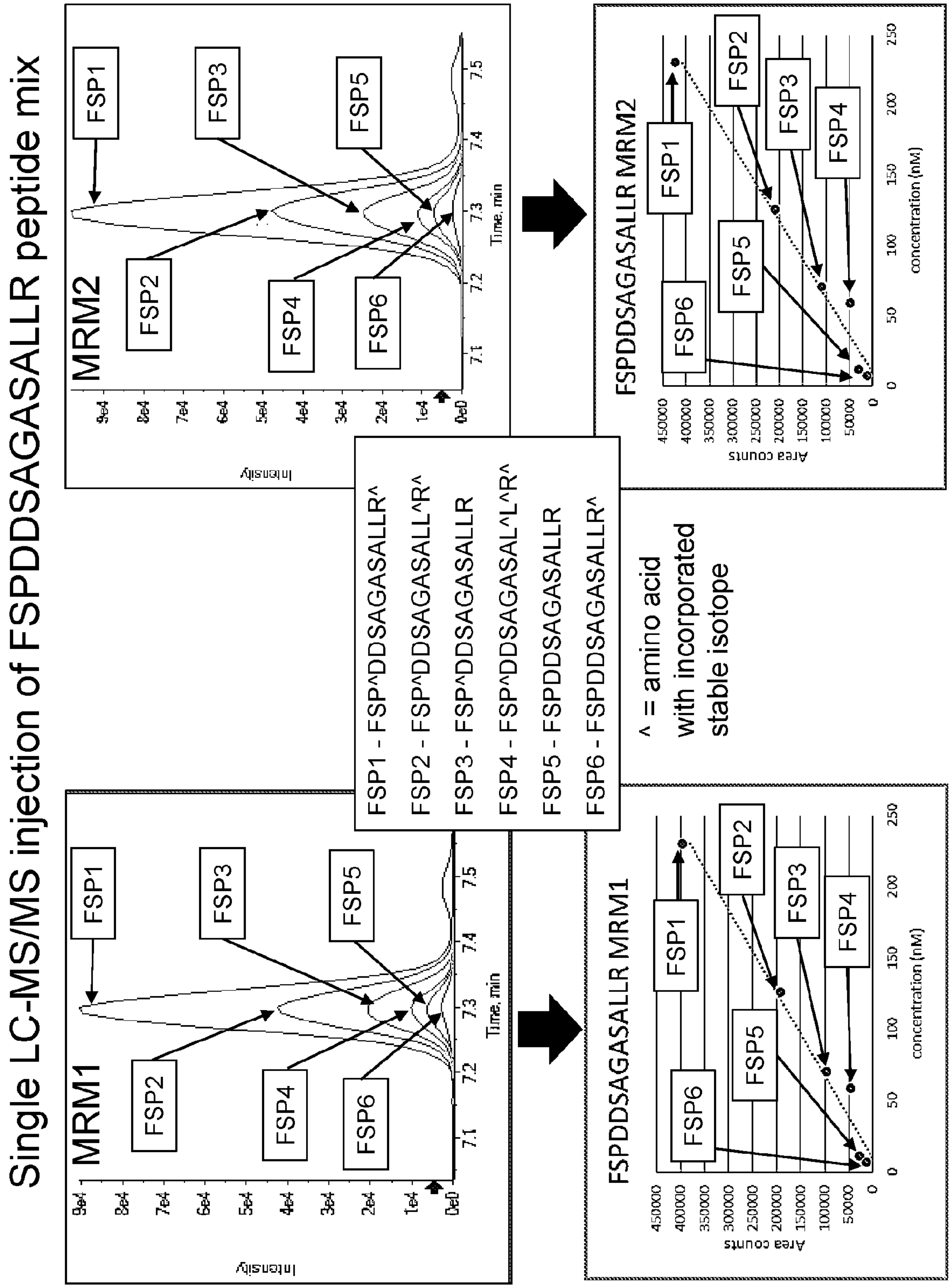
FIG. 12 depicts the XIC of the calibration mixture of FIG. 9 and the calibration curves generated therefrom for each peptide of FSPDDSAGASALLR based on the characteristic of MRM1 and MRM2 as an example of embodiments of the present application.

FIG. 9, on the other hand, depicts a set of calibrants for the peptide FSPDDSAGASALLR obtained by differentially labelling various amino acid positions, as well as two common fragmentation patterns to result in the detectable MRM transitions shown in FIG. 12. As shown in FIG. 9, for example, the precursor ion associated with the standard peptide FSPDDSAGASALLR exhibits a m/z of 703.9 and fragments to form y11 product ions having an m/z of 1075.5 (MRM1=703.9/1075.5) and y10 product ions having an m/z of 960.5 (MRM2=703.9/960.5). Additionally, as shown in FIG. 9, the peptide FSP^DDSAGASALLR exhibits the unique MRM1=706.9/1075.5 and the unique MRM2=706.9/960.5 for these y11 and y10, by way of example. It will again be observed that each of the MRM1 and MRM2 transitions are unique between the six calibrants for the target peptide FSPDDSAGASALLR such that a calibration curve (FIG. 12) may be generated independently based on either the MRM1 or MRM2 transition. Accordingly, in accordance with the present teachings, the same MRM transitions monitored for the standard peptide FSPDDSAGASALLR can be monitored while performing LC-MS/MS on a sample, with the resulting mass spectrometer signal compared to the calibration curves of FIG. 12 so as to quantify the target FSPDDSAGASALLR in the sample.

Finally, FIG. 13 depicts an exemplary method for measuring thyroglobulin in samples using a multiplexed calibration mixture comprising six calibrants (one standard and five isotopic analogs) for each of the peptides FSPDDSAGASALLR and VIFDANAPVAVR for a total of 12 calibrants. The procedure involves pre-treatment of the samples and calibration mixtures (i.e., addition of internal standard and reduction, alkylation, and trypsin digestion of thyroglobulin) followed by peptide enrichment and finally LC-MS/MS analysis. As shown in FIGS. 10 and 13, a mix of 12 peptides from New England Peptide (Gardner, MA) were mixed at the concentrations shown in 35% acetonitrile in water containing 0.1% formic acid and a 5 μL aliquot was subjected to LC-MS/MS analysis, with the 24 MRM channels shown in FIGS. 8 and 9 being utilized to identify the characteristic response associated with each of the calibrants relative to one another. Analysis was done using a SCIEX Topaz instrument equipped with a Kinetex C18 2.1×100 mm column with 2.6 μm particle size and 100 Å pore size using a solvent system comprising water with 0.1% formic acid as mobile phase A and acetonitrile with 0.1% formic acid as mobile phase B. The gradient used was: 2.5-25% B from 0-8.0 minutes, 25% B from 8-11.5 minutes, 25-2.5% B from 11.5-11.51 minutes and 2.5% B from 11.51-15 minutes. As shown, by providing this multiplexed calibration mixture for both peptides, instrument calibration time decreased by a factor of 11 relative to conventional external calibration techniques and successfully resulted in a calibration curves that could be used to quantify the particular peptides in a sample.

Example 3

Figure 14:
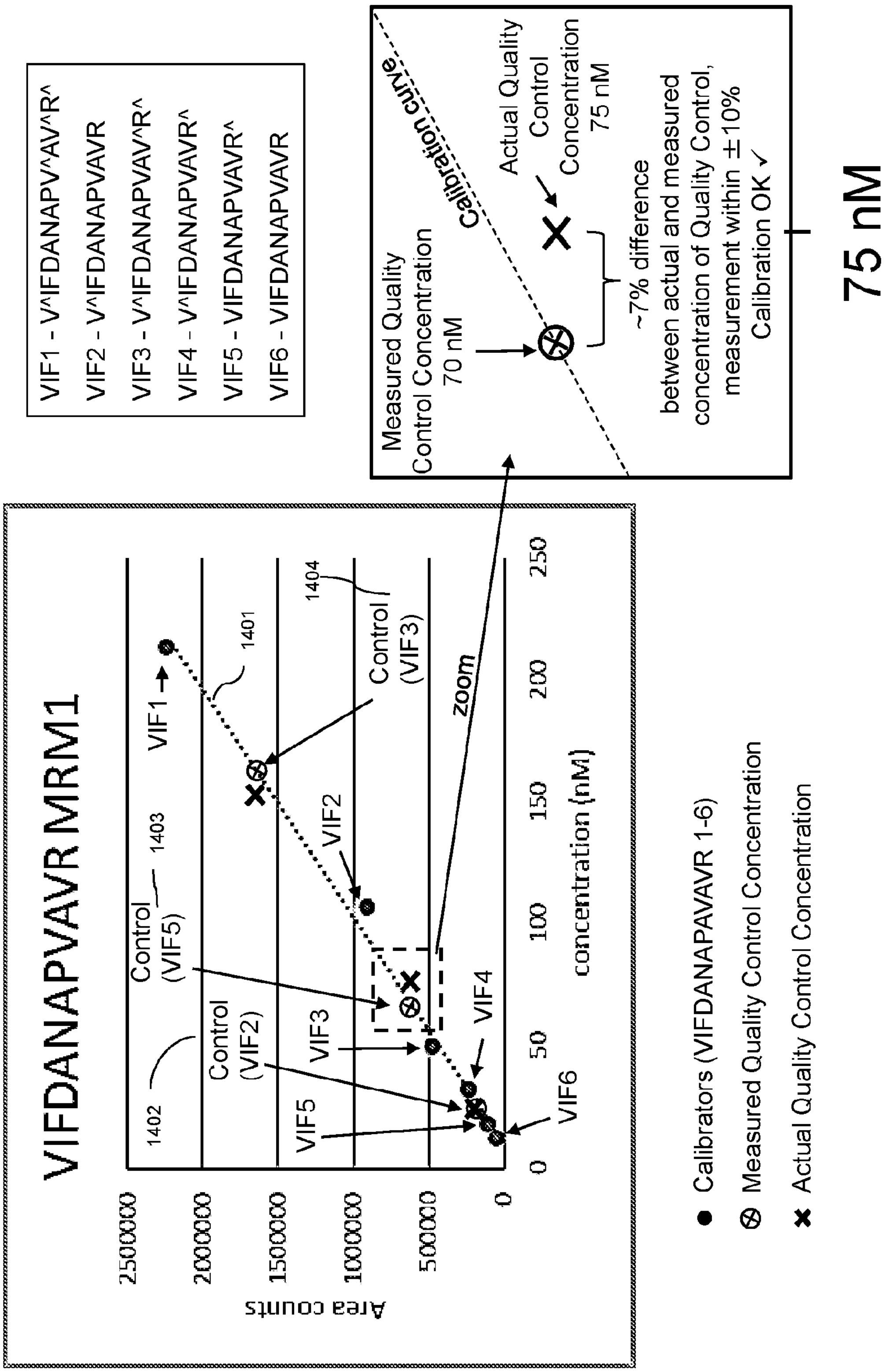
FIG. 14 schematically depicts an exemplary quality control process according to various aspects of the present teachings.

With reference now to FIG. 14, an exemplary protocol for validating a calibration curve is depicted. A calibration curve 1401 for VIFDANAPVAVR is created that correlates a characteristic response (e.g., area count) to a concentration. A quality control mixture comprising three different isotopic analogues of VIFDANAPVAVR, (V*IFDANAPVAVR 1402 VIFDANAPVAVR* 1403, and V*IFDANAPVAV*R* 1404 where * denotes an amino acid incorporated with stable isotope) present at three different concentrations (25, 75, 150 nM respectively) is created. This quality control sample is than analyzed using the procedure similar to that described in Example 2 and a quantity (or concentration) of each of the isotopic analogues is determined via mass spectrometry analysis and compared to the actual quantity (or concentration) known to be present for that isotopic analogue. As shown in the zoomed portion of FIG. 14, quality control 1403 having an actual concentration of 75 nM is determined by the mass spectrometer system and calibration curve 1401 to have a measured concentration of 70 nM. If the determined quantity/concentration is found to be outside of a predetermined threshold (e.g., ±10%), it is determined that a fault condition exists and the calibration must be repeated or other adjustments may be made to compensate for any discrepancy. In this example, since the difference between the actual and measured concentration for the VIF5 control 1403 is less than 10%, no adjustments or recalibration is needed.

Example 4

Figure 15:
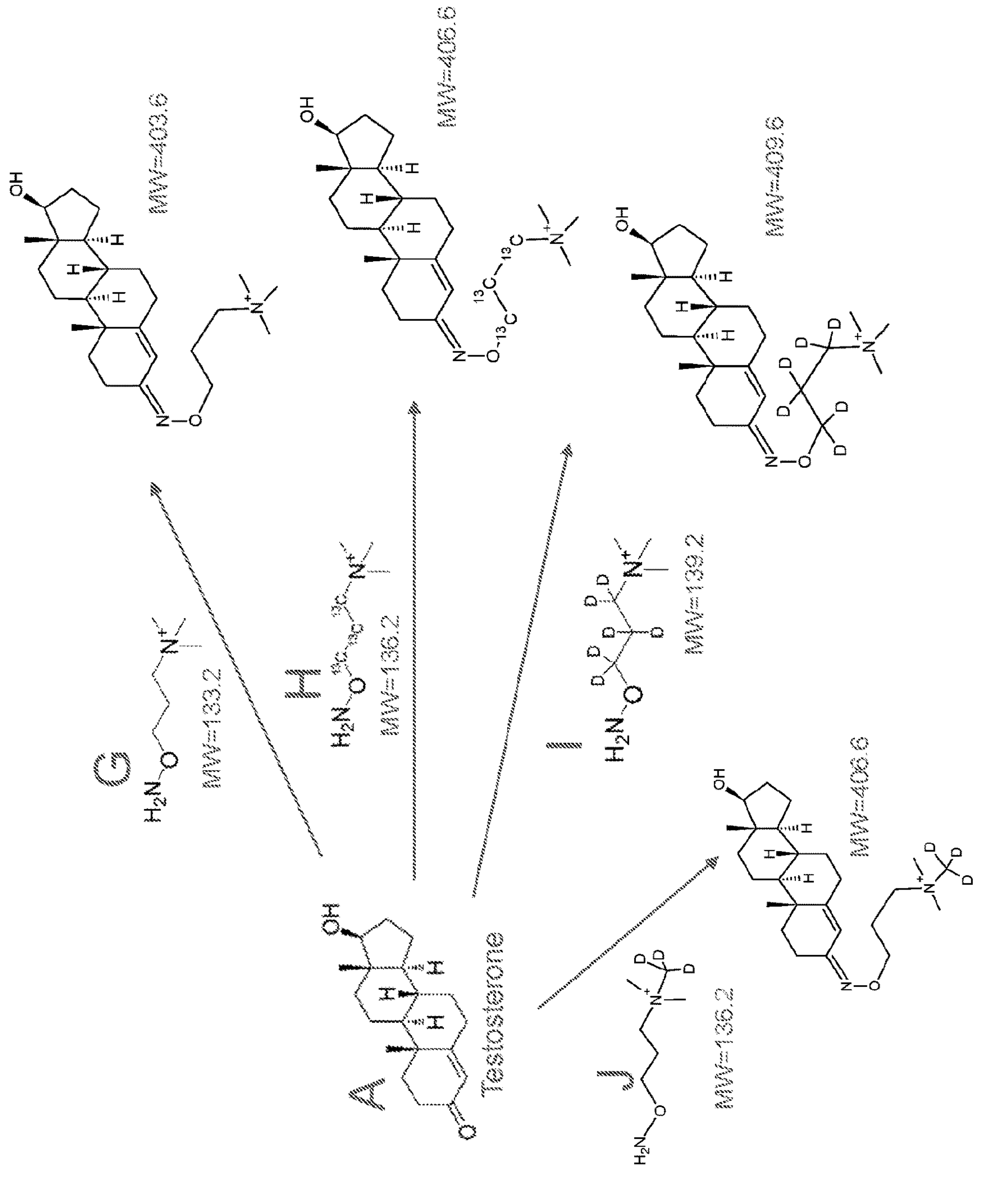
FIG. 15 schematically depicts an exemplary method of generating derivatized analytes that are distinguishable by mass spectrometry for testosterone when using isotopic variants of a derivatizing agent.

With reference now to FIG. 15, an exemplary method of generating calibrants using isotopic derivatizing agents is shown. In the depicted method, testosterone is reacted separately with one of three derivatizing agents that are based off of the Ampliflex ketone sold by Sciex. Derivatizing agent G having molecular weight of 133.2 is the same as the unmodified Ampliflex ketone reagent. Derivatizing agent H having molecular weight of 136.2 is a modified agent G, where the three carbon atom chain linking each end have been replaced with 13-carbon. Derivatizing agent I is a modification of compound G where the hydrogen atoms located on the carbons in the three carbon chain have been replaced with deuterium increasing the molecular weight to 139.2. Derivatizing Agent J is a modification of agent G where one set of hydrogens on a methyl substituted on the quaternary ammonium group has been replaced with deuteriums. As would be appreciated while two specific modifications to create compound H and I have been indicated here, other variations would be well within the scope of the person of ordinary skill in the art. For example, it is possible to modify only one or two of the carbon atoms in derivatizing agent H, rather than all three. Another example would be to modify compound I so that less than six of the hydrogens, but at least one are replaced with deuterium. In addition, other atoms within the structure can be replaced including other carbons, hydrogens, nitrogen, etc. in the derivatizing agent. In addition, the modifications need not be limited to only one type of modification. For example, incorporation of both 13-carbon and deuterium in a derivatizing agent may be utilized. Upon reaction with testosterone, each of the derivatizing agents produces a unique calibrant that has a different molecular weight (either before or after fragmentation) and is therefore distinguishable by mass spectrometry, but otherwise has identical physical and chemical properties.

Each of the depicted derivatized analytes shown in FIG. 15 can be mixed together with known concentration into a single calibration mixture, optionally as part of a kit, and utilized in accordance with the present teachings.

Figure 16:
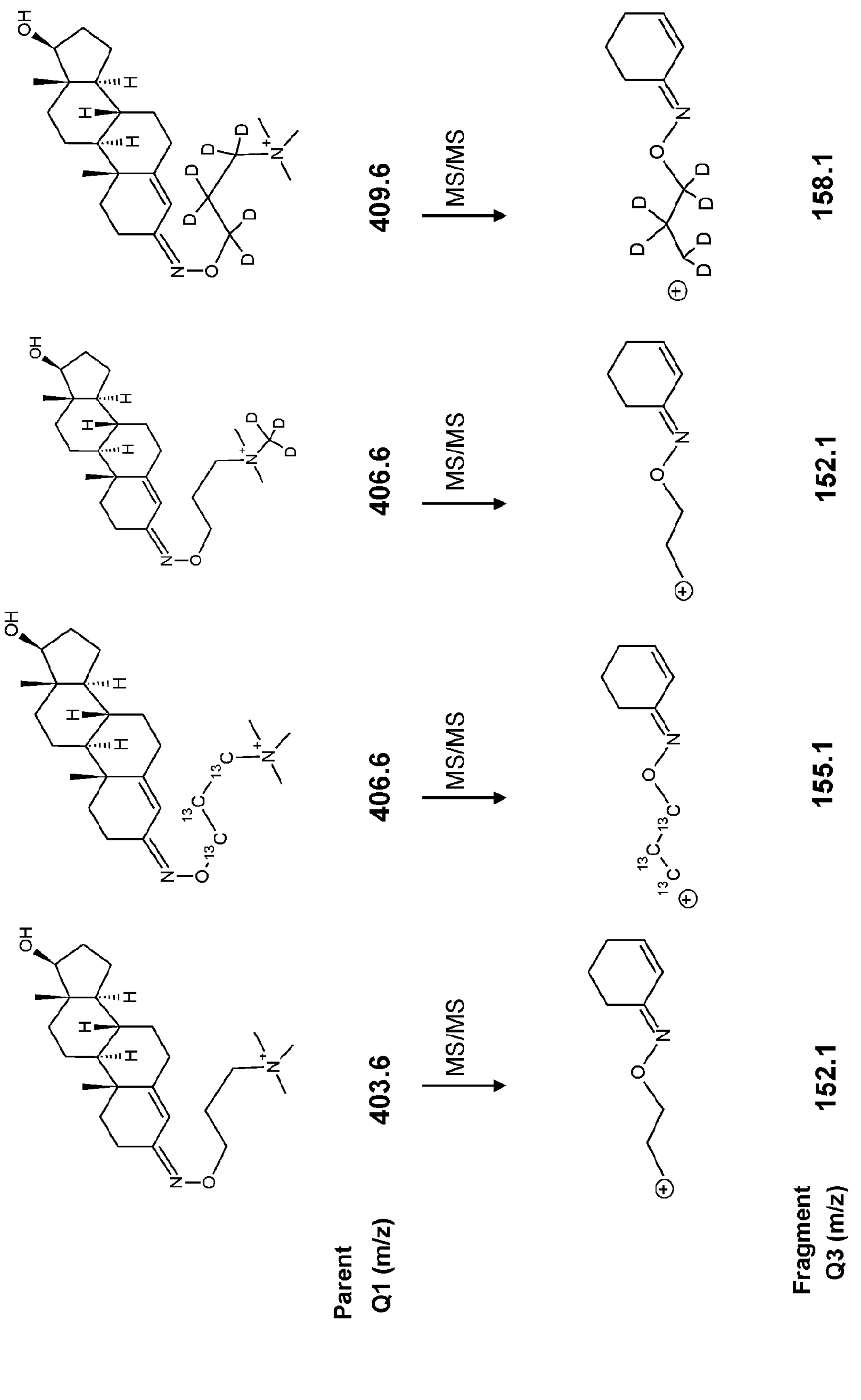
FIG. 16 schematically depicts the unique MRM signals that can be utilized to mass distinguish derivatized analytes.

FIG. 16 depicts the suitable MRM's for the detection of the derivatized testosterone analytes depicted in FIG. 15. As shown, either the precursor or fragment ion (or both) m/z value is unique to each derivatized analyte and is distinguishable in a MS/MS analysis. In cases were the parent ions may have similar m/z values (as in the case of the two derivatized analytes having m/z values of 406.6), it may be possible to distinguish between the two agents by use of an accurate mass analysis.

FIG. 17 depicts the various permutations that are possible using 6 different isotopic variants of an exemplary analyte, testosterone and 3 different isotopic variants of an exemplary derivatizing agent. A total of 18 different variations which are distinguishable by mass spectrometry exhibit substantially unique MRM signals and can be utilized in accordance with the present teachings.

Example 5

Testosterone (100 μg/mL in acetonitrile), 2,3,4-$^{13}C_3$-testosterone (10 μg/mL in acetonitrile), 16,16,17-$^{2}H_3$-testosterone (100 μg/mL in acetonitrile), and epi-testosterone (1 mg/mL in acetonitrile) were purchased from Cerilliant (Round Rock, TX). 2,2,4,6,6-$^{2}H_5$-testosterone and 3,4-$^{13}C_2$, 17-$^{18}O$-testosterone (both 100 μg/mL in methylene chloride) were purchased from CIL (Tewksbury, MA). 2,2,4,6,6,16, 16,17-$^{2}H_8$-testosterone (1 mg/mL in methanol) was purchased from IsoSciences (Ambler, PA). $ZnSO_4.7H_2O$ was purchased from Sigma Aldrich and prepared as a 0.4 M solution in ultra-pure water (18 MΩ Elga LabWater system, USA). LC/MS-grade methanol, acetonitrile, and formic acid were purchased from VWR (Radnor, PA). The IS solution was a solution of 20 ng/dL 2,3,4-$^{13}C_3$-testosterone in methanol. N-Methyl-2-pyrrolidone (NMP) and LC autosampler tubes and snap caps were purchased from VWR. Lyophilized bovine serum albumin (BSA) powder and ProClin™ 300 were purchased from Sigma Aldrich (St. Louis, MO). Standard Reference Material (SRM) 971, which contains testosterone, was purchased from the National Institute of Standards and Technology (NIST; Gaithersburg, MD). CDC serum samples (20 male and 22 female) were from the Hormone Standardization (HoSt) program (Atlanta, GA). The Amplifex™ Keto Reagent kit was obtained from SCIEX (Framingham, MA). The contents of the reagent vial and diluent vial were mixed 1:1 (V/V) prior to use to obtain the final Amplifex Keto Reagent solution. The system suitability solution (SST) was 1:1 (v/v) methanol:water containing derivatized forms of the following analytes: testosterone at 20 ng/dL, epi-testosterone at 6 ng/dL, and 2,3,4-$^{13}C_3$ testosterone at 10 ng/dL.

A 5% (wt/vol) BSA solution was made by first preparing a solution of 0.5% ProClin 300 in water (v/v), and then dissolving BSA in the 0.5% ProClin 300 solution (wt/v). Individual stock solutions of testosterone (9.0 μg/mL), 2,2, 4,6,6,16,16,17-$^{2}H_8$-testosterone (3.6 μg/mL), 16,16,17-$^{2}H_3$- testosterone (1 μg/mL), 3,4-$^{3}C_2$,17-$^{18}$O-testosterone (0.5 μg/mL), and 2,2,4,6,6-$^{2}H_5$-testosterone (0.1 μg/mL) were made in N-methyl-2-pyrrolidone. To make a batch of a single-tube calibrator, an aliquot from each stock solution was combined to make a spiking solution. A syringe pump (Harvard Apparatus, PHD 2000 Infusion) equipped with a syringe (Hamilton, Gastight #1750) loaded with the spike solution was used to add approximately 115 μL of the solution dropwise over 10 minutes to 20 mL of 5% BSA solution, which was in a round bottom flask being continually stirred with a magnetic stir bar. After addition of the spike solution, the batch was stirred for an additional 15 minutes, aliquoted into 1.5 mL cryovials, and stored at −20° C. until use. The single-tube calibrator batch was assigned values traceable to NIST SRM 971, and these concentrations are listed in Table 1.

TABLE 1

Final concentrations of analytes in the single-tube calibrator.

| Analyte | Concentration (ng/dL) |
|---|---|
| 2,2,4,6,6-$^{2}H_5$-testosterone | 4.2 |
| 3,4-$^{13}C_2$, 17-$^{18}$O-testosterone | 19.5 |
| 16,16,17-$^{2}H_3$-testosterone | 192.7 |
| 2,2,4,6,6,16,16,17-$^{2}H_8$-testosterone | 472.3 |
| Testosterone | 1096.8 |

In addition, multiple-tube calibrators were made that consisted of 7-level calibrators with each concentration being present in individual tubes. The concentrations spanned the concentration range of approximately 2-1800 ng/dL in 5% BSA with concentration values traceable to NIST SRM 971.

The following was added to a 1.5 mL microcentrifuge tube for each sample or calibrator: 85 μL final Amplifex Keto reagent solution, 25 μL precipitation solution ($ZnSO_4$ 0.4 M), 25 μL IS solution, and 100 μL of the serum sample or calibrator. After vortex mixing for 15-30 seconds, the sample was incubated for 30 minutes at room temperature, followed by centrifugation for 2 minutes at 15,000 rpm. The supernatant was transferred to an autosampler vial (polypropylene with 300 μL insert) for LC-MS/MS analysis.

Prepared samples were analyzed on a SCIEX Triple Quad™ 4500 LC-MS/MS System (Framingham, MA) and Shimadzu (Kyoto, Japan) Prominence liquid chromatography system consisting of 2 pumps (LC-20AD), an autosampler (LC-20AC HT), a column oven (20AC CL) and a system controller (CBM-20A). The injection volume was 50 μL for each unknown sample, calibrator, and SST. The SST was injected in triplicate prior to sample analysis to qualify the LC-MS/MS system performance. The LC gradient allowed for baseline separation of the geometric isomers of the Amplifex keto-testosterone formed after derivatization. The method MRM transitions for the derivatized testosterone isotopologues are listed in Table 2. For all MRM transitions, the methods used the following optimized MS settings: ion source gas 1 (GS1) at 50 PSI, ion source gas 2 (GS1) at 55 PSI, declustering potential (DP) of 85 V, ion spray voltage of 3000 V, cell exit potential (CXP) of 10 V, exit potential (EP) of 10 V, temperature of 650° C., and curtain gas (CUR) at 25 psi. All of the optimized collision energy voltages were within the range of 57-60 V.

TABLE 2

MRM transitions. (AK represents the Amplifex ketone derivative of the analyte)

| Analyte | MRM transition (Q1/Q3) |
|---|---|
| AK-(testosterone) | 403/164 |
| AK-(2,3,4-$^{13}C_3$-testosterone) | 406/167 |
| AK-(16,16,17-$^{2}H_3$-testosterone) | 406/164 |
| AK-(2,2,4,6,6-$^{2}H_5$-testosterone) | 408/168 |
| AK-(3,4-$^{13}C_2$, 17-$^{18}$O-testosterone) | 407/166 |
| AK-(2,2,4,6,6,16,16,17-$^{2}H_8$-testosterone) | 411/168 |

Injections of the CDC test samples were bracketed by injections of multiple-tube and single-tube calibrators, resulting in two injections of each type of calibrator and one injection of the CDC test samples. The peak area for each target analyte was the sum of the peak areas for both geometric isomers. All calibration curves were plots of the ratio of analyte peak area/IS peak area versus the ratio of calibrator concentration/IS concentration and the linear regression was weighted 1/x. The multiple-tube calibrator data were processed using MultiQuant™ (SCIEX, Framingham, MA) software and the single-tube calibrator data was processed using a development (beta) version of MultiQuant software that allowed the use of different MRM transitions for different calibrator levels. The analyte/IS ratios of peak areas obtained for the CDC samples with MultiQuant were then converted to measured testosterone concentrations using the linear regression equations generated by both the multiple-tube and single-tube calibrators in Excel. Passing-Bablok and Bland-Altman plots were made using Analyse It.

The LC-MS/MS testosterone assay employing the 7-level, multiple-tube calibrators used in this study qualified (Phase 1) for the CDC HoSt standardization program and continued as a certified participant in the program (Phase 2) in 2018. During both phases, serum samples are analyzed by the participant and the results are then compared by the CDC to the results generated by their reference method. The biases (mean % difference) between the results should be within the acceptance criteria of ±6.4%. The participating testosterone assay is comprised of reagents, the assay protocol, and the LC-MS/MS method. Therefore, to show that the single-tube calibrator can provide high-quality results, the single-tube calibrator was substituted into the assay and used to measure the testosterone concentration in 42 Phase 2 samples provided by the CDC as part of the HoSt program. These same 42 samples were analyzed by the testosterone assay using the normal 7-level, multiple-tube calibrators. Their results were compared to evaluate the performance of the single-tube calibrator versus the multiple-tube calibrator.

The calibration curves constructed from the data generated by analysis of the single-tube calibrator and multiple-tube calibrator demonstrated good linearity ($r^2$>0.999). The calibration equations for the 1/x-weighted calibration curves were y=0.0179x+0.0090 for the single-tube calibrator data and y=0.0201x+0.0023 for the multiple-tube calibrator data.

Figure 18:
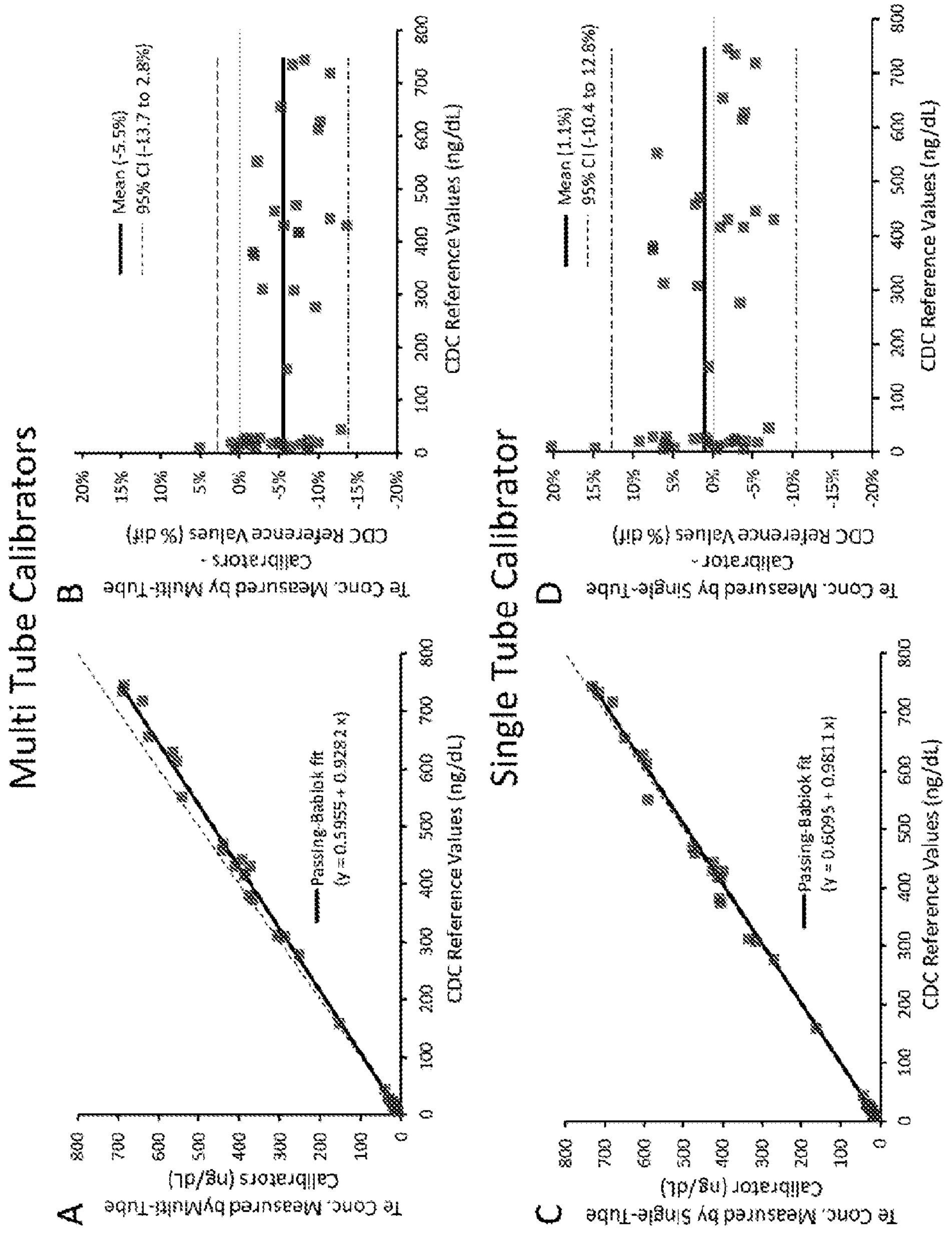
FIG. 18 shows a demonstration of a single tube calibrator system in comparison to multi-tube calibrator and the CDC reference method.

The testosterone concentrations measured in the 42 CDC samples using the single-tube calibration curve and the CDC reference method are compared in the Passing-Bablok plot in Panel C of FIG. 18. Panel A of FIG. 18 shows a similar comparison but using the testosterone concentrations measured using the calibration curve from the multiple-tube calibrators and the CDC reference method. For each plot, the solid line represents the best-fit line between the two data sets for the CDC samples and the dotted line represents the y=x line (i.e., a slope of 1 means the two methods generate equal results). The slopes of the single-tube and multiple-tube best-fit curves were 0.9811 and 0.9282, respectively, indicating that both methods performed similar to the CDC reference method. Panel D of FIG. 18 shows the Bland-Altman plot of the percent differences between testosterone concentrations measured in the 42 CDC samples using the single-tube calibrator and the CDC reference method. Panel B of FIG. 18 shows a similar comparison between the testosterone concentrations measured using the multiple-tube calibrators and the CDC reference method. The thin, gray lines in panels B and D of FIG. 18 represents the 0% difference used as a gauge to estimate the magnitude of the percent difference for the test data versus the reference represented by the black line. The dotted lines in panels B and D of FIG. 18 represent the 95% confidence intervals (CI) of the calculated bias. Here, the average percent differences (biases) for the single-tube calibrator and multiple-tube calibrator versus the CDC reference method are +1.1% and −5.5%, respectively, which are both within the CDC bias acceptance criteria of ±6.4%.

Those skilled in the art will know or be able to ascertain using no more than routine experimentation, many equivalents to the embodiments and practices described herein. By way of example, the dimensions of the various components and explicit values for particular electrical signals (e.g., amplitude, frequencies, etc.) applied to the various components are merely exemplary and are not intended to limit the scope of the present teachings. Accordingly, it will be understood that the invention is not to be limited to the embodiments disclosed herein, but is to be understood from the following claims, which are to be interpreted as broadly as allowed under the law.

The section headings used herein are for organizational purposes only and are not to be construed as limiting. While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

The invention claimed is:

1. A method of quantifying a target analyte in a series of samples by mass spectrometry, the method comprising:

obtaining a mass spectrometer signal for a calibration mixture, wherein the calibration mixture comprises a plurality of calibrants comprising at least a standard of the target analyte at a known target concentration in the calibration mixture, a first isotopic analog of the target analyte at a known first concentration, and a second isotopic analog of the target analyte at a known second concentration, wherein said plurality of calibrants are distinguishable by mass spectrometry from one another and have different, known concentrations from one another in said calibration mixture;

adding an internal standard to the calibration mixture and to each of said series of samples prior to obtaining the mass spectrometer signal for the calibration mixture and each of the series of samples, wherein the internal standard comprises a third isotopic analog at a third known concentration of the target analyte distinguishable by mass spectrometry from the standard of the target analyte, the first isotopic analog, and the second isotopic analog, wherein each of the first, second, and third isotopic analogs of the target analyte has a substantially same physiochemical properties as the target analyte, with at least one atom in each of the first, second, and third isotopic analogs being a different isotope of the corresponding at least one atom of the other isotopic analogs and of the standard of the target analyte;

identifying from the mass spectrometer signal for the calibration mixture a characteristic response of each of said plurality of calibrants, wherein each of the characteristic responses is associated with a different m/z value corresponding to a different one of the plurality of calibrants and being indicative of the concentration of each of the plurality of calibrants in the calibration mixture;

generating a single calibration curve for the calibration mixture based on said characteristic responses of the at least the standard of the target analyte, the first isotopic analog of the target analyte, the second isotopic analog of the target analyte, and the internal standard comprising the third isotopic analog of the target analyte;

obtaining a mass spectrometer signal from each of the series of samples;

identifying from the mass spectrometer signal for each sample a target analyte characteristic response indicative of an unknown concentration of the target analyte in the respective each sample, and a characteristic response indicative of the known third concentration of the internal standard comprising the third isotopic analog of the target analyte added to the respective sample; and comparing the characteristic response of the target analyte in the each sample to the single calibration curve to quantify the unknown concentration of the target analyte in the respective each sample.

2. The method of claim 1, wherein the calibration mixture comprises different, known concentrations of each of the standard, the first isotopic analog, and the second isotopic analog, and wherein each of the standard, the first isotopic analog, and the second isotopic analog is distinguishable by mass spectrometry from the others.

3. The method of claim 2, wherein the calibration mixture comprises at least a fourth isotopic analog of the target analyte, wherein the fourth isotopic analog is at a different, known concentration and is distinguishable by mass spectrometry from the standard, the first isotopic analog, the second isotopic analog, and the internal standard comprises the third isotopic analog.

4. The method of claim 3, wherein the concentration of the heaviest isotopic analog in the calibration mixture is less than the concentration of the other of said isotopic analogs of said target analyte in the calibration mixture and wherein the concentration of the lightest isotopic analog in the calibration mixture is greater than the concentration of the other of said isotopic analogs of said target analyte in the calibration mixture.

5. The method of claim 1, further comprising preparing the calibration mixture by combining a known quantity of each of the plurality of calibrants.

6. The method of claim 1, further comprising adding the calibration mixture to a surrogate sample matrix prior to obtaining the mass spectrometer signal for the calibration mixture.

7. The method of claim 6, further comprising separating the plurality of calibrants from the surrogate sample matrix prior to obtaining the mass spectrometer signal for the calibration mixture.

8. The method of claim 7, wherein the separation comprises at least one of solid phase extraction, liquid-liquid extraction, liquid chromatography, gas chromatography, supercritical fluid chromatography, affinity, immunoaffinity, and capillary electrophoresis.

9. The method of claim 7, further comprising derivatizing the plurality of calibrants prior to the separation.

10. The method of claim 1, wherein the calibration mixture further comprises a set of second calibrants for a second target analyte different from the target analyte, wherein the set of second calibrants comprise at least two of a standard of the second target analyte, a first isotopic analog of the second target analyte, and a second isotopic analog of the second target analyte, wherein said second calibrants are distinguishable by mass spectrometry from one another and have different, known concentrations from one another in said calibration mixture and wherein each of said second calibrants are distinguishable by mass spectrometry from said plurality of calibrants, the method further comprising:

identifying from the mass spectrometer signal for the calibration mixture a characteristic response of each of said second calibrants, wherein each of the characteristic responses correspond to a different one of the second calibrants and is indicative of the concentration of the second calibrants in the calibration mixture;

generating a second calibration curve based on said characteristic responses of said second calibrants;

identifying from the mass spectrometer signal for each sample a characteristic response indicative of the concentration of the second target analyte in each sample; and comparing the characteristic response of the second target analyte in each sample to the second calibration curve to quantify the second target analyte in each sample.

11. The method of claim 1, wherein each characteristic response comprises a cumulative intensity of the mass spectrometer signal.

12. The method of claim 1, wherein the mass spectrometer signal exhibits an intensity for each m/z, and wherein each characteristic response comprises a separate intensity peak of the mass spectrometer signal for at least one unique m/z corresponding to each of the plurality of calibrants.

13. The method of claim 1, wherein obtaining a mass spectrometer signal for the calibration mixture comprises:

ionizing the calibrants or derivatives thereof;

separating the ionized calibrants or derivatives thereof based on their mass-to-charge ratios (m/z); and detecting the m/z-separated ionized calibrants or derivatives thereof, wherein each of the ionized calibrants or derivatives thereof exhibit a unique m/z ratio relative to the other of the ionized calibrants or derivatives thereof.

14. The method of claim 1, wherein obtaining a mass spectrometer signal for the calibration mixture comprises:

ionizing the calibrants or derivatives thereof within the calibration mixture;

fragmenting each of the ionized calibrants or derivatives thereof; and detecting at least one fragment of each of the ionized calibrants or derivatives thereof, wherein each of the ionized calibrants or derivatives thereof exhibit at least one unique MRM transition relative to the other of said ionized calibrants or derivatives thereof.

15. The method of claim 1 wherein at least one of the series of samples comprises a quality control, the quality control comprising a second plurality of calibrants selected from the group comprising a standard of the target analyte, a first isotopic analog of the target analyte, and a second isotopic analog of the target analyte, wherein said second plurality of calibrants are distinguishable by mass spectrometry from one another and have different, known concentrations from one another in said quality control.

16. A method of quantifying a target analyte in a series of samples by mass spectrometry, the method comprising:

obtaining a mass spectrometer signal for a calibration mixture, wherein the calibration mixture comprises a plurality of calibrants comprising at least a standard of the target analyte reacted with a first derivatizing agent, the target analyte reacted with a second derivatizing agent, and the target analyte reacted with a third derivatizing agent, the first, second and third derivatizing agents being isotopic analogues of one another and wherein said plurality of calibrants are distinguishable by mass spectrometry from one another and have different, known concentrations from one another in said calibration mixture;

adding an internal standard to the calibration mixture and each of said series of samples prior to obtaining the mass spectrometer signal for the calibration mixture and each of the series of samples, wherein the internal standard comprises the target analyte reacted with a fourth derivatizing agent comprising a fourth isotopic analog of the first, second, and third derivatizing agents distinguishable by mass spectrometry from the first derivatizing agent, the second derivatizing agent, and the third derivatizing agent, with the internal standard of the target analyte having a fourth concentration different than the respective concentrations of the plurality of calibrants, wherein each of the first, second, third, and fourth derivatizing agents has a substantially same physiochemical properties, with at least one atom in each of the first, second, third, and fourth derivatizing agents being a different isotope of the corresponding at least one atom of the other derivatizing agents;

identifying from the mass spectrometer signal for the calibration mixture a characteristic response of each of said plurality of calibrants, wherein each of the characteristic responses is associated with a different m/z value corresponding to a different one of the plurality of calibrants and being indicative of the concentration of each of the plurality of calibrants in the calibration mixture;

generating a single calibration curve for the calibration mixture based on said characteristic responses of the standard of the target analyte reacted with the first derivatizing agent, the target analyte reacted with the second derivatizing agent, the target analyte reacted with the third derivatizing agent, and the internal standard comprising target analyte reacted with the fourth derivatizing agent;

creating a derivatized sample for each of the series of samples by reacting each of the series of samples with one of the first derivatizing agent, the second derivatizing agent, the third derivatizing agent or an isotopic analog thereof;

obtaining a mass spectrometer signal from each of the derivatized samples from the series of samples;

identifying from the mass spectrometer signal for each of the derivatized samples from the series of samples a characteristic response indicative of an unknown concentration of the target analyte in each derivatized sample, and a characteristic response indicative of the known fourth concentration of the internal standard comprising the target analyte reacted with the fourth derivatizing agent; and comparing the characteristic response of each of the derivatized samples in the series of samples to the single calibration curve to quantify the unknown concentration of the target analyte in each sample.

17. The method of claim 16 wherein the target analyte is a ketone or carboxylic acid containing analyte and the first, second or third derivatizing agent is selected from the group consisting of:

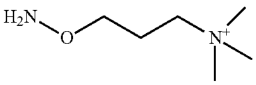
,
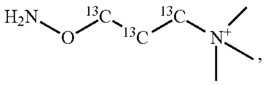
,
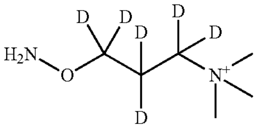
, and
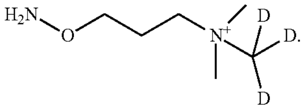

18. A method of quantifying an analyte in a series of samples by mass spectrometry, the method comprising:

obtaining a mass spectrometer signal for a calibration mixture, wherein the calibration mixture comprises a plurality of calibrants comprising at least a first compound at a known target concentration in the calibration mixture, a first isotopic analog of the first compound at a known first concentration, and a second isotopic analog of the first compound at a known second concentration, wherein each of the first compound and the first and second isotopic analogs of the first compound are distinguishable by mass spectrometry from one another and have different, known concentrations from one another in said calibration mixture, adding an internal standard to the calibration mixture and each of said series of samples prior to obtaining the mass spectrometer signal for the calibration mixture and each of the series of samples, wherein the internal standard comprises a third isotopic analog of the first compound at a third known concentration distinguishable by mass spectrometry from the first compound, the first isotopic analog, and the second isotopic analog, wherein each of the first, second, and third isotopic analogs of the first compound has a substantially same physiochemical properties as the first compound, with at least one atom in each of the first, second, and third isotopic analogs being a different isotope of the corresponding at least one atom of the other isotopic analogs and of the standard of the first compound;

identifying from the mass spectrometer signal for the calibration mixture a characteristic response of each of said plurality of calibrants, each of the characteristic responses is associated with a different m/z value corresponding to a different one of the plurality of calibrants and being indicative of the concentration of each of the plurality of calibrants in the calibration mixture;

generating a single calibration curve for the calibration mixture based on said characteristic responses of the at least the first compound, the first isotopic analog of the first compound, the second isotopic analog of the first compound, and the internal standard comprising the third isotopic analog of the first compound;

obtaining a mass spectrometer signal from each of the series of samples, each of the series of samples containing a target analyte having the same structure as the first compound or an isotopic analog of the first compound;

identifying from the mass spectrometer signal for each sample a first compound characteristic response indicative of an unknown concentration of the target analyte in the respective each sample, and a characteristic response indicative of the known third concentration of the internal standard comprising the third isotopic analog of the first compound added to the respective sample; and comparing the characteristic response of the target analyte in each sample to the single calibration curve to quantify the unknown concentration of the target analyte in the respective each sample.

19. The method of claim 18 wherein each of the plurality of calibrants comprises a reaction product of a molecule that is being tested for and a derivatizing agent and wherein each of the derivatizing agents utilized for each of the plurality of calibrants is an isotopic analog of the other derivatizing agents, and optionally wherein the molecule that is being tested for is testosterone, a peptide or a hormone.

20. The method of claim 12, wherein the unique m/z corresponding to each of the plurality of calibrants comprises the m/z of a fragment ion for each of the plurality of calibrants.

* * * * *